US009181274B2

(12) United States Patent
Gushurst et al.

(10) Patent No.: US 9,181,274 B2
(45) Date of Patent: Nov. 10, 2015

(54) FORMS OF RIFAXIMIN AND USES THEREOF

(71) Applicants: Karen S. Gushurst, West Lafayette, IN (US); Donglai Yang, Annandale, NJ (US); Melanie Janelle Bevill, West Lafayette, IN (US); Nathan Carl Schultheiss, Lafayette, IN (US); Giuseppe Claudio Viscomi, Bologna (IT)

(72) Inventors: Karen S. Gushurst, West Lafayette, IN (US); Donglai Yang, Annandale, NJ (US); Melanie Janelle Bevill, West Lafayette, IN (US); Nathan Carl Schultheiss, Lafayette, IN (US); Giuseppe Claudio Viscomi, Bologna (IT)

( * ) Notice: Subject to any disclaimer, the term of this patent is extended or adjusted under 35 U.S.C. 154(b) by 213 days.

(21) Appl. No.: 13/644,241

(22) Filed: Oct. 3, 2012

(65) Prior Publication Data

US 2014/0011828 A1  Jan. 9, 2014

Related U.S. Application Data

(63) Continuation of application No. 13/368,917, filed on Feb. 8, 2012, now abandoned, which is a continuation of application No. 13/165,410, filed on Jun. 21, 2011, now abandoned, which is a continuation of application No. 12/676,756, filed on Mar. 5, 2010, now abandoned, which is a continuation-in-part of application No. PCT/US2009/035192, filed on Feb. 25, 2009.

(60) Provisional application No. 61/031,329, filed on Feb. 25, 2008.

(51) Int. Cl.
*C07D 498/18* (2006.01)
*C07D 498/16* (2006.01)

(52) U.S. Cl.
CPC ............ *C07D 498/18* (2013.01); *C07D 498/16* (2013.01)

(58) Field of Classification Search
CPC ........................... A61K 31/485; C07D 498/18
USPC .......................................... 514/279; 540/457
See application file for complete search history.

(56) References Cited

U.S. PATENT DOCUMENTS

| 4,341,785 | A | 7/1982 | Marchi et al. |
| 4,557,866 | A | 12/1985 | Cannata et al. |
| 7,045,620 | B2 | 5/2006 | Viscomi et al. |
| 7,612,199 | B2 | 11/2009 | Viscomi et al. |
| 7,709,634 | B2 | 5/2010 | Kothakonda et al. |
| 7,906,542 | B2 | 3/2011 | Viscomi et al. |
| 7,915,275 | B2 | 3/2011 | Viscomi et al. |
| 8,067,429 | B2 | 11/2011 | Gushurst et al. |
| 8,486,956 | B2 | 7/2013 | Gushurst et al. |
| 8,569,326 | B2 | 10/2013 | Gushurst et al. |
| 8,754,098 | B2 | 6/2014 | Gushurst et al. |
| 2005/0272754 | A1 | 12/2005 | Viscomi et al. |
| 2006/0019986 | A1 | 1/2006 | Ding et al. |
| 2006/0210592 | A1 | 9/2006 | Kodsi |
| 2008/0132530 | A1 | 6/2008 | Viscomi et al. |
| 2008/0262012 | A1 | 10/2008 | Viscomi et al. |
| 2008/0262024 | A1* | 10/2008 | Viscomi et al. ................ 514/294 |
| 2008/0262220 | A1 | 10/2008 | Viscomi et al. |
| 2008/0262232 | A1 | 10/2008 | Viscomi et al. |
| 2009/0011020 | A1 | 1/2009 | Viscomi et al. |
| 2009/0082558 | A1 | 3/2009 | Kothakonda et al. |
| 2009/0130201 | A1 | 5/2009 | Viscomi et al. |
| 2009/0312357 | A1 | 12/2009 | Rao et al. |
| 2009/0324736 | A1 | 12/2009 | Johnson et al. |
| 2010/0136125 | A1 | 6/2010 | Jacobus et al. |
| 2011/0086871 | A1* | 4/2011 | Viscomi et al. ................ 514/279 |
| 2012/0035202 | A1* | 2/2012 | Viscomi et al. ................ 514/279 |
| 2012/0289532 | A1* | 11/2012 | Lavagna et al. ................ 514/279 |

FOREIGN PATENT DOCUMENTS

| CN | 1886408 | 12/2006 |
| CN | 1900077 A | 1/2007 |
| CN | 101031572 | 9/2007 |
| EP | 0161534 A2 | 11/1985 |
| EP | 1557421 A1 | 7/2005 |
| EP | 1698630 A1 | 9/2006 |
| EP | 2257557 A2 | 12/2010 |
| IT | MI2005A000345 | 3/2005 |
| JP | 2003519698 A | 6/2003 |
| JP | 2005139161 A | 6/2005 |
| JP | 2007509904 A | 4/2007 |
| RU | 2403015 C2 | 11/2010 |
| WO | 2005044823 A2 | 5/2005 |
| WO | 2006/094737 A2 | 9/2006 |
| WO | 2006094662 A1 | 9/2006 |
| WO | 2008035109 A1 | 3/2008 |
| WO | 2008155728 A1 | 12/2008 |
| WO | 2009008005 A1 | 1/2009 |
| WO | 2009047801 A1 | 4/2009 |
| WO | 2009108730 A2 | 9/2009 |
| WO | 2010033179 A1 | 3/2010 |

(Continued)

OTHER PUBLICATIONS

Rossi, C. et al., "NMR Investigation of a New Semisynthetic Bioactive Compound," Bulletin of Magnetic Resonance, 1996, vol. 18, No. 1-2, pp. 87-90.
Viscomi, G. et al., "Crystal Forms of Rifaximin and Their Effect on Pharmaceutical Properties," CrystEngComm, 2008, 10, 1074-1081.
Brufani, M. et al., "X-Ray Crystal Structure of 4-Deoxy-3'-bromopyrido[1,2'-1,2]imidazo[5,4-c]rifamycin S," The Journal of Antibiotics, 37(12):1623-1627 (Dec. 1984).
Database CA [Online] Chemical Abstracts Service, Columbus, Ohio, US; Marcon, Giuliano: "Crystalline form of rifaximin and method of preparation" XP002637581, retrieved from STN Database accesion No. 2009:1314795 & IT 200 5MI 034 A1 (Solmag S.P.A., Italy) May 18, 2011.

(Continued)

*Primary Examiner* — Raymond Henley, III
(74) *Attorney, Agent, or Firm* — McCarter & English LLP; Jonathan M. Sparks; Michael J. DeGrazia

(57) ABSTRACT

The present invention relates to Rifaximin amorphous forms, to their use in medicinal preparations and to therapeutic methods using them.

7 Claims, 16 Drawing Sheets

(56) References Cited

FOREIGN PATENT DOCUMENTS

| | | | |
|---|---|---|---|
| WO | 2010067072 | A1 | 6/2010 |
| WO | 2011051971 | A2 | 5/2011 |
| WO | 2011/153444 | A1 | 12/2011 |
| WO | 2011/156897 | A2 | 12/2011 |
| WO | 2012/109605 | A2 | 8/2012 |

OTHER PUBLICATIONS

Italian Product Label for NORMIX (rifaximin), Apr. 23, 1985.
US Package Insert for XIFAXAN (rifaximin) Mar. 2008.
Database CA [Online] Chemical Abstracts Service, Columbus, Ohio, US; Viscomi, Guiseppe Claudio et al, "New polymorphous forms of rifaximin for pharmaceuticals" XP002696258, Jun. 11, 2012.

* cited by examiner

FORMS OF RIFAXIMIN AND USES THEREOF

RELATED APPLICATIONS

This application is a continuation of U.S. application Ser. No. 13/368,917, filed on Feb. 8, 2012, now abandoned, which is a continuation of U.S. application Ser. No. 13/165,410, filed on Jun. 21, 2011, now abandoned, which is a continuation of U.S. application Ser. No. 12/676,756, filed on Mar. 5, 2010, now abandoned, which is a continuation-in-part of PCT/US2009/035192, filed Feb. 25, 2009, which claims the benefit of U.S. Provisional Application No.: 61/031,329, filed Feb. 25, 2008. The entire contents of each of these applications are expressly incorporated herein by reference.

BACKGROUND

Rifaximin (INN; see The Merck Index, XIII Ed., 8304) is an antibiotic belonging to the rifamycin class of antibiotics, e.g., a pyrido-imidazo rifamycin. Rifaximin exerts its broad antibacterial activity, for example, in the gastrointestinal tract against localized gastrointestinal bacteria that cause infectious diarrhea, irritable bowel syndrome, small intestinal bacterial overgrowth, Crohn's disease, and/or pancreatic insufficiency. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

Rifaximin is described in Italian Patent IT 1154655 and EP 0161534, both of which are incorporated herein by reference in their entirety for all purposes. EP 0161534 discloses a process for rifaximin production using rifamycin O as the starting material (The Merck Index, XIII Ed., 8301). U.S. Pat. No. 7,045,620 B1 and PCT Publication WO 2006/094662 A1 disclose polymorphic forms of rifaximin.

Rifaximin is approved for the treatment of pathologies caused by non-invasive strains of *Escherichia coli*, a microorganism which is not able to penetrate into GI mucosa and therefore remains in contact with gastrointestinal fluids.

SUMMARY

Described herein are polymorphic and amorphous forms of rifaximin not previously described. Form Amorphous forms of rifaximin are described herein.

According to one aspect, a polymorph amorphous forms exhibits an X-ray powder diffraction pattern having characteristic peaks expressed in degrees 2θ (+/−0.20 degree θ) at 7.3 (approximate halo maximum), 11.3-17.8 (amorphous halo range), and 15.8 (approximate halo maximum) degrees 2-θ; or 5.1-10.1 (amorphous halo range), 11.3-17.8 (amorphous halo range), and 15.8 (approximate halo maximum) degrees 2-θ; or 5.1-10.1 (amorphous halo range), 7.3 (approximate halo maximum), and 11.3-17.8 (amorphous halo range) degrees 2-θ; or 5.1-10.1 (amorphous halo range), 7.3 (approximate halo maximum), and 15.8 (approximate halo maximum) degrees 2-θ; or 5.1-10.1 (amorphous halo range), 7.3 (approximate halo maximum), 11.3-17.8 (amorphous halo range), 15.8 (approximate halo maximum) degrees 2-θ.

According to one aspect, a polymorph amorphous forms exhibits an X-ray powder diffraction pattern having characteristic peaks expressed in degrees 2θ (+/−0.20 degree θ) at 7.3 (approximate halo maximum), 11.3-17.8 (amorphous halo range), and 15.8 (approximate halo maximum) degrees 2-θ.

According to one aspect, a polymorph amorphous forms exhibits an X-ray powder diffraction pattern having characteristic peaks expressed in degrees 2θ (+/−0.20 degree θ) at 5.1-10.1 (amorphous halo range), 11.3-17.8 (amorphous halo range), and 15.8 (approximate halo maximum) degrees 2-θ.

According to one aspect, a polymorph amorphous forms exhibits an X-ray powder diffraction pattern having characteristic peaks expressed in degrees 2θ (+/−0.20 degree θ) at 5.1-10.1 (amorphous halo range), 7.3 (approximate halo maximum), and 11.3-17.8 (amorphous halo range) degrees 2-θ.

According to one aspect, a polymorph amorphous forms exhibits an X-ray powder diffraction pattern having characteristic peaks expressed in degrees 2θ (+/−0.20 degree θ) at 5.1-10.1 (amorphous halo range), 7.3 (approximate halo maximum), and 15.8 (approximate halo maximum) degrees 2-θ.

According to one aspect, a polymorph amorphous forms exhibits an X-ray powder diffraction pattern having characteristic peaks expressed in degrees 2θ (+/−0.20 degree θ) at 5.1-10.1 (amorphous halo range), 7.3 (approximate halo maximum), 11.3-17.8 (amorphous halo range), 15.8 (approximate halo maximum) degrees 2-θ.

In one embodiment, the amorphous forms exhibits thermogravimetric analyses (TGA) of a 1.5% weight loss at 100° C.

In one embodiment, the polymorph exhibits Differential Scanning calorimetry (DSC) of a broad endotherm at about 78° C. and a minor endotherm at 203° C.

In one embodiment, polymorph amorphous forms exhibits Modulated Differential Scanning calorimetry (MDSC) shows a glass transition (Tg) temperature onset to be about 199° C.

In one embodiment, the composition further comprises one or more pharmaceutically acceptable excipients. The excipients may be one or more of a diluting agent, binding agent, lubricating agent, disintegrating agent, coloring agent, flavoring agent or sweetening agent.

According to one embodiment, the pharmaceutical composition may be formulated as coated or uncoated tablets, hard or soft gelatin capsules, sugar-coated pills, lozenges, wafer sheets, pellets or powders in a sealed packet. In a related embodiment, the pharmaceutical composition may also be formulated for topical use.

According to another aspect, provided herein are methods of treating, preventing or alleviating a bowel related disorder comprising administering to a subject in need thereof an effective amount of amorphous form of rifaximin.

In one embodiment, the subject is suffering from at least one bowel related disorder selected from the group consisting of irritable bowel syndrome, travelers' diarrhea, small intestinal bacterial overgrowth, Crohn's disease, chronic pancreatitis, pancreatic insufficiency, enteritis and colitis.

In another embodiment, the EtOH slurry comprises an EtOH/H$_2$O slurry in the ratio of from between 1 to 0.02-0.45.

Provided herein, according to one aspect, are processes for producing a mixture of polymorphs ζ and γ comprising humidifying Form ζ.

Provided herein, according to one aspect, are processes for producing amorphous rifaximin comprising grinding Form γ or a mixture of Form γ and Form η of rifaximin.

According to one aspect, provided herein are processes for producing amorphous rifaximin comprising crash precipitation from ethyl acetate with heptane.

In one embodiment, the process further comprises milling the produced amorphous rifaximin.

According to one aspect, provided herein are processes for producing amorphous rifaximin comprising lyophilization in p-dioxane:water 1:1, and fast evaporation from acetone.

In one embodiment, the process further comprises milling the produced amorphous rifaximin.

According to one aspect, provided herein are processes for producing amorphous rifaximin comprising precipitation from acetone.

In one embodiment, the process further comprises milling the produced amorphous rifaximin.

According to one aspect, provided herein are processes for producing amorphous rifaximin comprising precipitating the initial rifaximin forms in the manner set forth in Table 7.

According to one aspect, provided herein are processes for producing amorphous Form of rifaximin comprising precipitating the initial forms in the manner set forth in Tables 20-22.

Provided herein, according to one aspect, are kits for treating a bowel disorder in a subject, comprising amorphous form of rifaximin and instructions for use.

Provided herein, according to one aspect, are packaged compositions comprising, a therapeutically effective amount of amorphous form of rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

In one aspect, a pharmaceutical composition is presented, which comprises amorphous form of rifaximin and a pharmaceutically acceptable carrier.

In one embodiment, the pharmaceutical composition further comprises excipients.

According to another embodiment, the excipients are one or more of a diluting agent, binding agent, lubricating agent, disintegrating agent, coloring agent, flavoring agent or sweetening agent.

In another embodiment, the composition is formulated for selected coated and uncoated tablets, hard and soft gelatine capsules, sugar-coated pills, lozenges, wafer sheets, pellets and powders in sealed packets.

In one embodiment, the composition is formulated for topical use.

Presented herein, according to one aspect, are methods of treating, preventing, or alleviating a bowel related disorder comprising administering to a subject in need thereof a cell infected with a virus with an effective amount of amorphous form of rifaximin.

According to another embodiment, wherein the bowel related disorder is one or more of irritable bowel syndrome, travelers' diarrhea, small intestinal bacterial overgrowth, Crohn's disease, chronic pancreatitis, pancreatic insufficiency, or colitis.

Presented herein, according to one aspect, are methods of assessing the efficacy of a bowel related disorder treatment in a subject, monitoring the progress of a subject being treated for a bowel related disorder, or a method of selecting a subject for treatment of a bowel disorder, comprising:

determining a pre-treatment level of bacterial overgrowth;

administering a therapeutically effective amount of amorphous form of rifaximin to the subject; and determining a post-treatment level of bacterial overgrowth after an initial period of treatment with the amorphous form of rifaximin.

In one embodiment, the modulation of the level of bacterial overgrowth indicates efficacy of the treatment.

In another embodiment, a decrease in bacterial overgrowth indicates that the treatment is efficacious.

In another embodiment, the modulation of the bacterial overgrowth is an indication that the subject is likely to have a favorable clinical response to the treatment.

Presented herein, according to one aspect, are kits for treating a bowel disorder in a subject, comprising one or more actions for use.

Also presented herein, according to one aspect are packaged compositions comprising a therapeutically effective amount of amorphous form of rifaximin and a pharmaceutically acceptable carrier or diluents, wherein the composition is formulated for treating a subject suffering from or susceptible to a bowel disorder, and packaged with instructions to treat a subject suffering from or susceptible to a bowel disorder.

Also presented herein is the use of one or more amorphous forms of rifaximin as a medicament.

Presented herein, according to another aspect, are processes for the production of one amorphous form of rifaximin.

Presented herein, according to another aspect, is a Form amorphous of rifaximin comprising an XRPD pattern substantially similar to FIG. 1.

Presented herein, according to another aspect, is a Form amorphous of rifaximin comprising a TGA and a DSC substantially similar to FIG. 2.

Presented herein, according to another aspect, is a Form amorphous of rifaximin comprising an XRPD pattern substantially similar to FIG. 4.

Presented herein, according to another aspect, is a Form amorphous of rifaximin comprising a DSC substantially similar to FIG. 6.

Presented herein, according to another aspect, is a Form amorphous of rifaximin comprising a cycling DSC substantially similar to FIG. 7.

Presented herein, according to another aspect, is a Form amorphous of rifaximin comprising a TG substantially similar to FIG. 8.

Presented herein, according to another aspect, is an amorphous Form of rifaximin comprising a cycling DSC substantially similar to FIG. 10.

Presented herein, according to another aspect, is a Form amorphous of rifaximin comprising a TG substantially similar to FIG. 11.

Presented herein, according to another aspect, is a Form amorphous of rifaximin comprising a cycling DSC substantially similar to FIG. 13.

Presented herein, according to another aspect, is a Form amorphous of rifaximin comprising a TG substantially similar to FIG. 14.

Presented herein, according to another aspect, is a Form amorphous of rifaximin comprising a modulated DSC substantially similar to FIG. 15.

Presented herein, according to another aspect, is a Form amorphous of rifaximin comprising a modulated DSC substantially similar to FIG. 16.

Other embodiment and aspects are disclosed infra.

DETAILED DESCRIPTION

Figure 1:
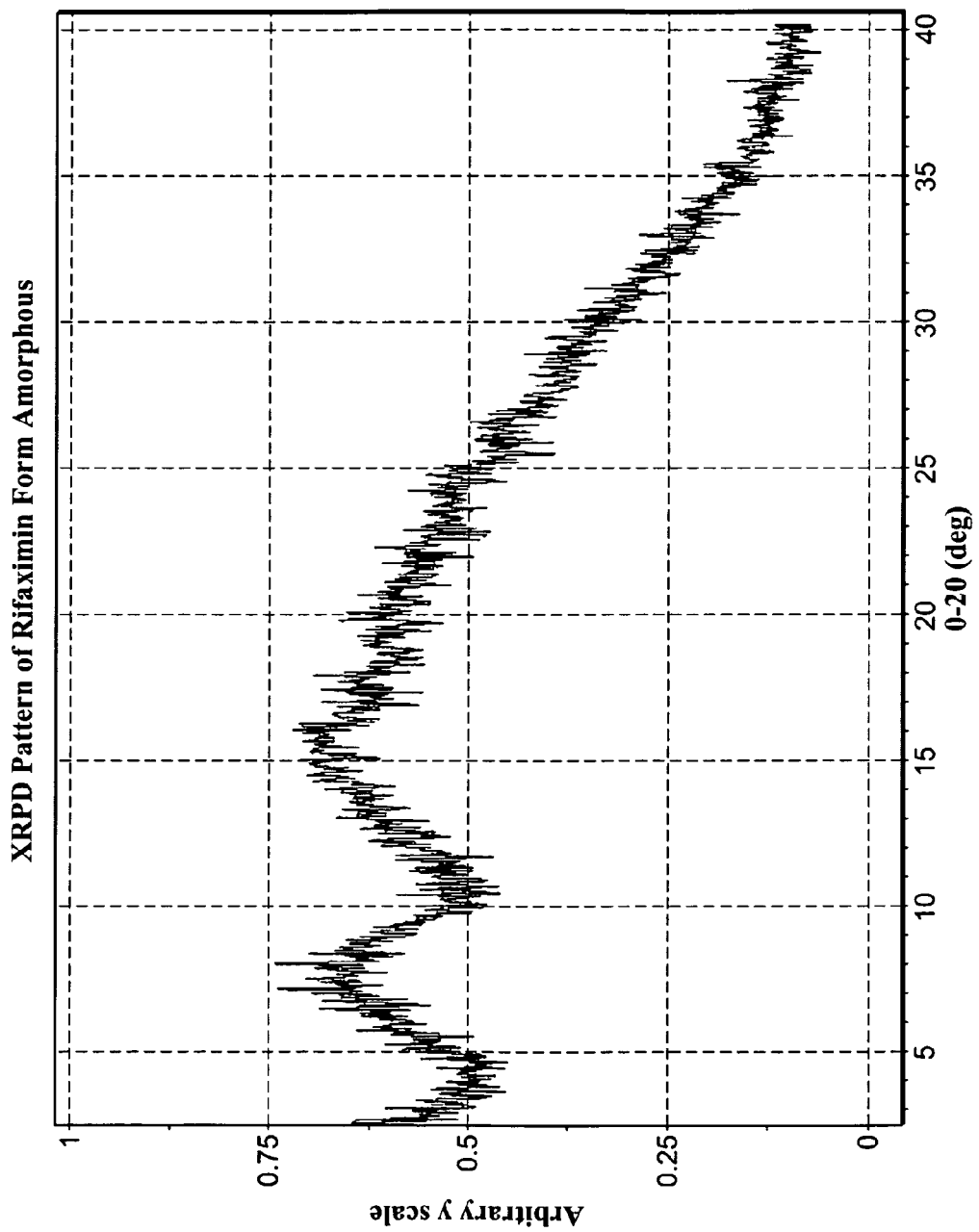
FIG. 1 is an exemplary XRPD pattern of rifaximin form amorphous.

Embodiments of the invention relate to the discovery of new polymorphic forms of rifaximin and the use of those forms as antibiotics. In one embodiment the use of amorphous forms (FIGS. 1-3, 4, and 5-16) of the antibiotic known as Rifaximin (INN), in the manufacture of medicinal preparations for the oral or topical route is contemplated. Embodiments of the invention also relate to administration of such medicinal preparations to a subject in need of treatment with antibiotics.

Rifaximin is a compound of the rifamycin class of antibiotics. Rifaximin is a compound having the structure of Formula I:

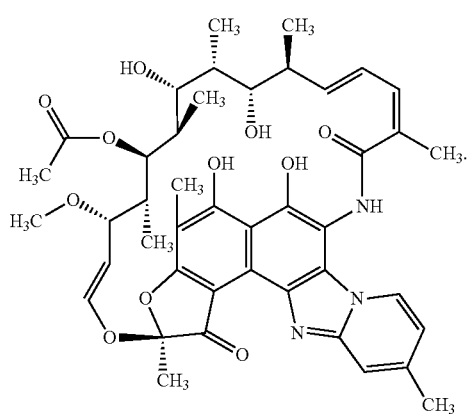

As used herein, "rifaximin Form ζ," "Form ζ" "Form ζ of rifaximin," "polymorph ζ," and "rifaximin ζ" are used interchangeably to denote the polymorphic form of rifaximin as further described herein by, for example, one or more peaks of an x-ray diffractogram, differential scanning calorimetry data. Form ζ comprises an x-ray powder diffraction pattern peak positions at about 4.7 (doublet), 7.6 (doublet), and 9.5 degrees 2-θ; or at about 4.7 (doublet), 7.3, and 8.2 degrees 2-θ; or at about 7.6 (doublet), 8.6, and 10.5 degrees 2-θ; or at about 8.2, 8.6, and 9.5 degrees 2-θ; or at about 10.2 (triplet), 12.6 (quintet), and 13.2 (doublet) degrees 2-θ; or at about 7.3, 10.5, and 12.9 (doublet) degrees 2-θ; or at about 7.3, 7.6 (doublet), 8.2, 8.6 degrees 2-θ; or at about 4.7 (doublet), 7.3, 7.6 (doublet), 9.5, and 10.5 degrees 2-θ; or at about 8.2, 8.6, 9.5, 10.2 (triplet), and 10.5 degrees 2-θ; or at about 8.6, 9.5, 10.2 (triplet), 10.5, and 11.2 (doublet) degrees 2-θ; or at about 4.7 (doublet), 6.3, 6.4, 7.3, 7.6 (doublet), 8.2, 8.6, 9.5, 10.2 (triplet), 10.5, 11.2 (doublet), 11.9 (doublet), 12.2 (weak), 12.6 (quintet), 12.9 (doublet), 13.2 (doublet) degrees 2-θ. Form ζ may be identified and characterized by one or more of these parameters and/or one or more of the peaks or points in the ranges.

As used herein, "rifaximin Form η," "Form η," "polymorph η," "Form η of rifaximin" and "rifaximin η" are used interchangeably to denote the polymorphic form of rifaximin as further described herein by, for example, one or more peaks of an x-ray diffractogram and methods of making such form. Form η comprises x-ray powder diffraction pattern peak positions at about 6.1, 7.3, and 7.5 degrees 2-θ; or 6.1, 7.3, and 7.9 degrees 2-θ; or 6.1, 7.3, and 8.8 degrees 2-θ; or 6.1, 7.3, and 12.7 degrees 2-θ; or 6.1, 7.5, and 8.8 degrees 2-θ; or 6.1, 7.5, and 7.9 degrees 2-θ; or 5.3, 6.1, and 7.3 degrees 2-θ; or 5.3, 6.1, and 7.9 degrees 2-θ; or 5.3, 6.1, and 12.7 degrees 2-θ; or 5.3, 6.1, and 7.5 degrees 2-θ; or 5.3, 6.1, and 8.8 degrees 2-θ; or 6.1, 7.3, 7.5, 7.9, 8.8, and 12.7 degrees 2-θ; or 5.3, 6.1, 7.3, 7.5, 7.9, 8.8, 12.7 degrees 2-θ; or 5.3, 6.1, 7.3, 7.9, 8.8, and 12.7 degrees 2-θ; or 5.3, 6.1, 7.3, 7.5, 8.8, and 12.7 degrees 2-θ; or 5.3, 6.1, 7.3, 7.5, 7.9, 8.8, and 12.7 degrees 2-θ. Form η may be identified and characterized by one or more of these parameters and/or one or more of the peaks or points in the ranges.

As used herein, "rifaximin Form ι," "Form ι," "polymorph ι," "Form ι of rifaximin" and "rifaximin ι" are used interchangeably to denote the polymorphic form of rifaximin as further described herein by, for example, one or more peaks of an x-ray diffractogram, NMR, thermal data, or hot stage microscopy and methods of making such form. Form ι comprises x-ray powder diffraction pattern peak positions described above. Form ι may be identified and characterized by one or more of these parameters and/or one or more of the peaks or points in the ranges.

As used herein, "rifaximin mesylate Form," "Form mesylate," "polymorph mesylate," "Form mesylate of rifaximin" and "rifaximin mesylate" are used interchangeably to denote the polymorphic form of rifaximin as further described herein by, for example, one or more peaks of an x-ray diffractogram and methods of making such form. Mesylate Form comprises x-ray powder diffraction pattern peak positions described above. Mesylate Form may be identified and characterized by one or more of these parameters and/or one or more of the peaks or points in the ranges.

As used herein, "rifaximin Form amorphous," "Form amorphous," and "rifaximin amorphous" are used interchangeably to denote the amorphous forms of rifaximin formed from mechanical disruption of polymorphic forms of rifaximin as further described herein by, for example, one or more peaks of an x-ray diffractogram, including 7.3 (approximate halo maximum), 11.3-17.8 (amorphous halo range), and 15.8 (approximate halo maximum) degrees 2-θ; or 5.1-10.1 (amorphous halo range), 11.3-17.8 (amorphous halo range), and 15.8 (approximate halo maximum) degrees 2-θ; or 5.1-10.1 (amorphous halo range), 7.3 (approximate halo maximum), and 11.3-17.8 (amorphous halo range) degrees 2-θ; or 5.1-10.1 (amorphous halo range), 7.3 (approximate halo maximum), and 15.8 (approximate halo maximum) degrees 2-θ; or 5.1-10.1 (amorphous halo range), 7.3 (approximate halo maximum), 11.3-17.8 (amorphous halo range), 15.8 (approximate halo maximum) degrees 2-θ; (FIG. 1) dissolution, or differential scanning calorimetry data (FIG. 2), Form amorphous may be identified and characterized by one or more of these parameters and/or one or more of the peaks or points in the ranges. The amorphous form, as used herein, is encompassed by the general reference to rifaximin polymorphs or polymorphic forms of rifaximin. The amorphous forms may be indentified, for example, by XRPD, TG, DSC, modulated DSC, or FT-IR methods (FIGS. 1-4).

As used herein, the term polymorph is occasionally used as a general term in reference to the forms of rifaximin and includes within the context, salt, hydrate, polymorph and amorphous forms of rifaximin disclosed herein. This use depends on context and will be clear to one of skill in the art.

As used herein, the term "about" when used in reference to x-ray powder diffraction pattern peak positions refers to the inherent variability of the peaks depending on, for example, the calibration of the equipment used, the process used to produce the polymorph, the age of the crystallized material and the like, depending on the instrumentation used. In this case the measure variability of the instrument was about ±0.2 degrees 2-θ. A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word about.

Polymorphism, as used herein, refers to the occurrence of different crystalline forms of a single compound in distinct hydrate status, e.g., a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as solubility profiles, melting point temperatures, hygroscopicity, particle shape, density, flowability, compactibility and/or x-ray diffraction peaks. The solubility of each polymorph may vary, thus, identifying the existence of pharmaceutical polymorphs is essential for providing pharmaceuticals with predictable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, Pharm Manuf. 3, 33 (1986); J. K. Haleblian and W. McCrone, J. Pharm. Sci., 58, 911 (1969); and J. K. Haleblian, J. Pharm. Sci., 64, 1269 (1975), all of which are incorporated herein by reference.

As used herein, "subject" includes organisms which are capable of suffering from a bowel disorder or other disorder treatable by rifaximin or who could otherwise benefit from the administration of a rifaximin as described herein, such as human and non-human animals. Preferred human animals include human subjects. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a bowel disorder is meant to include subjects at risk of developing a bowel disorder infection, i.e., subjects suffering from immune suppression, subjects that have been exposed to other subjects with a bacterial infection, physicians, nurses, subjects traveling to remote areas known to harbor bacteria that causes travelers' diarrhea, etc.

The language "a prophylactically effective amount" of a compound refers to an amount of a compound of the invention of formula (I) or otherwise described herein which is effective, upon single or multiple dose administration to the subject, in preventing or treating a bacterial infection.

The language "therapeutically effective amount" of a compound of the invention refers to an amount of an agent which is effective, upon single or multiple dose administration to the subject to provide a therapeutic benefit to the subject. In one embodiment, the therapeutic benefit is inhibiting a virus, or in prolonging the survivability of a subject with such a viral infection. In another embodiment, the therapeutic benefit is inhibiting a bacterial infection or prolonging the survival of a subject with such a bacterial infection beyond that expected in the absence of such treatment.

Rifaximin exerts a broad antibacterial activity in the gastrointestinal tract against localized gastrointestinal bacteria that cause infectious diarrhea, including anaerobic strains. It has been reported that rifaximin is characterized by a negligible systemic absorption, due to its chemical and physical characteristics (Descombe J. J. et al. *Pharmacokinetic study of rifaximin after oral administration in healthy volunteers. Int J Clin Pharmacol Res,* 14 (2), 51-56, (1994)).

In respect to possible adverse events coupled to the therapeutic use of rifaximin, the induction of bacterial resistance to the antibiotics is of particular relevance.

From this point of view, any differences found in the systemic absorption of ζ, η or amorphous forms of rifaximin may be significant, because at sub-inhibitory concentration of rifaximin, such as in the range from 0.1 to 1 μg/ml, selection of resistant mutants has been demonstrated to be possible (Marchese A. et al. *In vitro activity of rifaximin, metronidazole and vancomycin against clostridium difficile and the rate of selection of spontaneously resistant mutants against representative anaerobic and aerobic bacteria, including ammonia-producing species. Chemotherapy,* 46(4), 253-266, (2000)).

Polymorphs of rifaximin have been found to have differing in vivo bioavailability properties. Thus, the polymorphs disclosed herein would be useful in the preparation of pharmaceuticals with different characteristics for the treatment of infections. This would allow generation of rifaximin preparations that have significantly different levels of adsorption with $C_{max}$ values from about 0.0 ng/ml to 5.0 μg/ml. This leads to preparation of rifaximin compositions that are from negligibly to significantly adsorbed by subjects undergoing treatment. One embodiment of the invention is modulating the therapeutic action of rifaximin by selecting the proper polymorphic form, or mixture of forms, for treatment of a patient. For example, in the case of invasive bacteria, the most bioavailable polymorphic form can be selected from those disclosed herein, whereas in case of non-invasive pathogens less adsorbed forms of rifaximin can be selected, since they may be safer for the subject undergoing treatment.

The above-mentioned amorphous forms can be advantageously used as pure and homogeneous products in the manufacture of medicinal preparations containing rifaximin.

Some features of a rifaximin amorphous forms include, for example:

Amorphous rifaximin (FIGS. 1-3) was prepared by milling Form γ or Form γ+η at ambient temperature. Amorphous rifaximin was physically stable under various relative humidities and exhibited a high glass transition temperature onset of 199° C.

For XRPD analysis, accuracy and precision associated with third party measurements on independently prepared samples on different instruments may lead to variability which is greater than ±0.1° 2Θ. For d-space listings, the wavelength used to calculate d-spacings was 1.541874 Å, a weighted average of the Cu-Kα1 and Cu-Kα2 wavelengths. Variability associated with d-spacing estimates was calculated from the USP recommendation, at each d-spacing, and provided in the respective data tables and peak lists.

Figure 2:
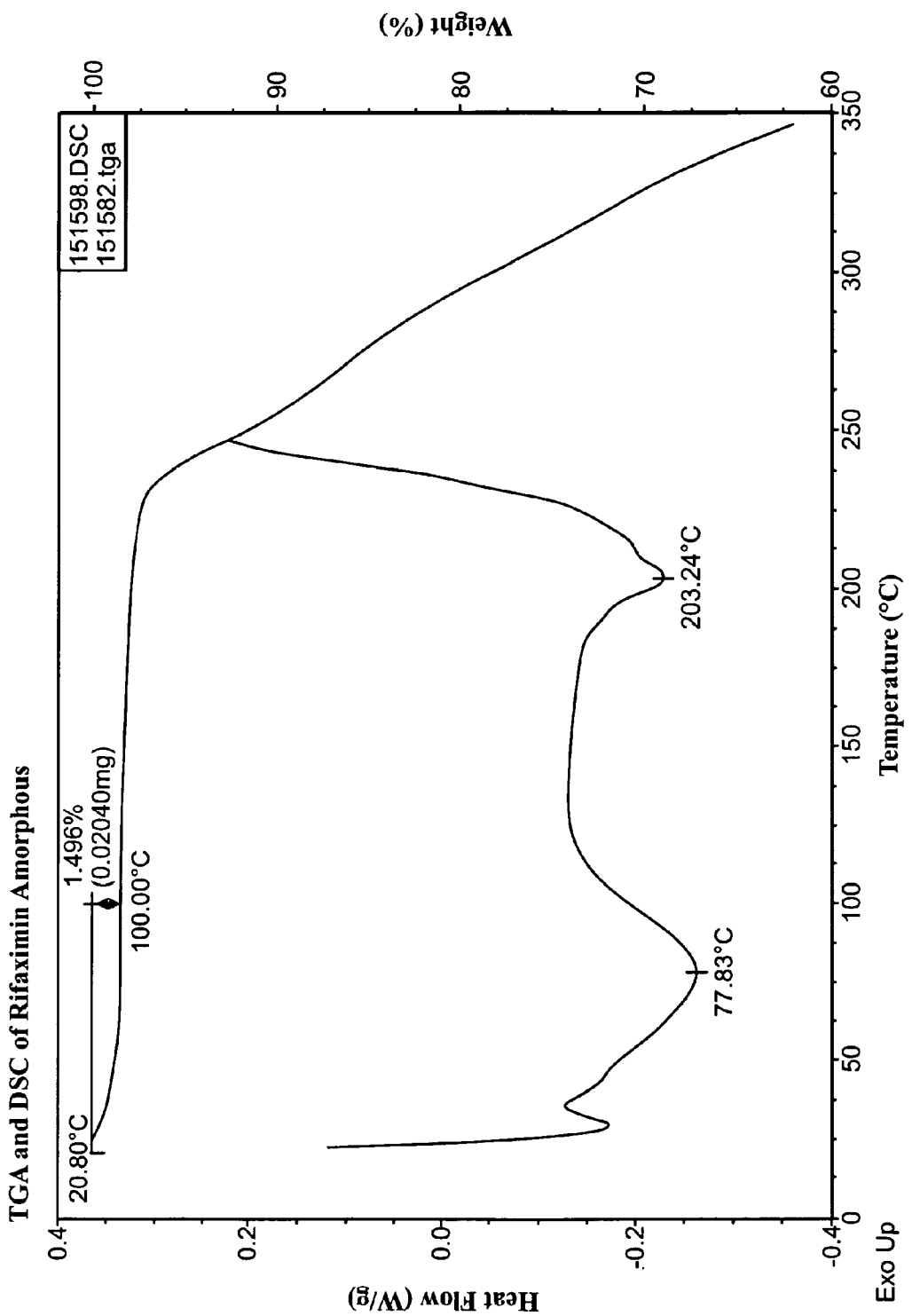
FIG. 2 shows an exemplary TGA and a DSC of rifaximin form amorphous.

Thermogravimetry (TG) analysis of amorphous rifaximin demonstrated a 1.5% weight loss to 100° C., accompanied by a broad endotherm at 78° C. in the DSC trace, indicating the material contained residual solvent. A minor endotherm at 203° C. was also observed in the DSC trace. Cyclic DSC was performed to dry the sample and determine the $T_g$, however the glass transition temperature was not apparent from the data. Modulated differential scanning calorimetry showed the glass transition ($T_g$) temperature onset to be approximately 199° C. (FIG. 2). Amorphous rifaximin was hygroscopic gaining 11.6% weight under 95% RH. The gained weight was lost during the desorption cycle. The post moisture balance XRPD pattern was amorphous.

The behavior of amorphous rifaximin under various relative humidities was also investigated. Amorphous material was stored under 43% RH for 5 days, 58% RH for 8 days and 75% RH for 2 days. The material remained amorphous by XRPD analysis.

Amorphous rifaximin may also be obtained by spray-drying, fluid bed and ball mill crushing as further described below.

Methods of Treatment

Provided herein are methods of treating, preventing, or alleviating bowel related disorders comprising administering to a subject in need thereof an effective amount of amorphous form polymorph of rifaximin. Bowel related disorders include one or more of irritable bowel syndrome, diarrhea, microbe associated diarrhea, *Clostridium difficile* associated diarrhea, travelers' diarrhea, small intestinal bacterial overgrowth, Crohn's disease, chronic pancreatitis, pancreatic insufficiency, enteritis, colitis, hepatic encephalopathy, or pouchitis.

The length of treatment for a particular bowel disorder will depend in part on the disorder. For example, travelers' diarrhea may only require treatment duration of 12 to about 72 hours, while Crohn's disease may require treatment durations from about 2 days to 3 months. Dosages of rifaximin will also vary depending on the diseases state. Proper dosage ranges are provided herein infra.

Provided herein are methods of treating or preventing a pathology in a subject suspected of being exposed to a biological warfare agent.

The identification of those subjects who are in need of prophylactic treatment for bowel disorder is well within the ability and knowledge of one skilled in the art. Certain of the methods for identification of subjects which are at risk of developing a bowel disorder which can be treated by the subject method are appreciated in the medical arts, such as family history, travel history and expected travel plans, the presence of risk factors associated with the development of that disease state in the subject. A clinician skilled in the art can readily identify such candidate subjects, by the use of, for example, clinical tests, physical examination and medical/family/travel history.

A method of assessing the efficacy of the treatment in a subject includes determining the pre-treatment level of intestinal bacterial overgrowth by methods well known in the art (e.g., hydrogen breath testing, biopsy, sampling of the intestinal bacteria, etc.) and then administering a therapeutically effective amount of a rifaximin polymorph to the subject. After an appropriate period of time (e.g., after an initial period of treatment) from the administration of the compound, e.g., 2 hours, 4 hours, 8 hours, 12 hours, or 72 hours, the level of bacterial overgrowth is determined again. The modulation of the bacterial level indicates efficacy of the treatment. The level of bacterial overgrowth may be determined periodically throughout treatment. For example, the bacterial overgrowth may be checked every few hours, days or weeks to assess the further efficacy of the treatment. A decrease in bacterial overgrowth indicates that the treatment is efficacious. The method described may be used to screen or select subjects that may benefit from treatment with a rifaximin polymorph.

In yet another aspect, a method of treating a subject suffering from or susceptible to a bowel disorder comprises administering to a subject in need thereof a therapeutically effective amount of a rifaximin polymorph described herein, to thereby treat the subject. Upon identification of a subject suffering from or susceptible to a bowel disorder, for example, IBS, one or more rifaximin polymorphs are administered.

In one aspect, methods of assessing the efficacy of treatment with a rifaximin polymorph in a subject comprise determining the pre-treatment level of bacterial overgrowth, administering a therapeutically effective amount of a rifaximin polymorph to the subject, and determining the bacterial overgrowth after an initial period of treatment with a rifaximin polymorph, wherein the modulation of the bacterial overgrowth indicates efficacy of an anti-bacterial treatment.

Efficacy of a treatment may be measured for example, as reduction of bacterial overgrowth. Efficacy may also be measured in terms of a reduction of symptoms associated with the bowel disorder, a stabilization of symptoms, or a cessation of symptoms associated with a bowel disorder, for example, a reduction of nausea, bloating, diarrhea, and the like.

In one aspect, methods of monitoring the progress of a subject being treated with a rifaximin polymorph comprise determining the pre-treatment level of bacterial overgrowth, administering a therapeutically effective amount of a rifaximin polymorph to the subject, and determining the bacterial overgrowth after an initial period of treatment with a rifaximin polymorph, wherein the modulation of the bacterial overgrowth indicates efficacy of an antibacterial treatment.

Pharmaceutical Preparations

Embodiments also provide pharmaceutical compositions, comprising an effective amount of a rifaximin polymorph (e.g., Form ζ, Form η, Form α-dry, Form ι, Form β-1, Form β-2, Form ε-dry, mesylate Form or amorphous forms) described herein and a pharmaceutically acceptable carrier. In a further embodiment, the effective amount is effective to treat a bacterial infection, e.g., small intestinal bacterial overgrowth, Crohn's disease, hepatic encephalopathy, antibiotic associated colitis, and/or diverticular disease.

For examples of the use of rifaximin to treat Travelers' diarrhea, see Infante R M, Ericsson C D, Zhi-Dong J, Ke S, Steffen R, Riopel L, Sack D A, DuPont, H L. Enteroaggregative *Escherichia coli* Diarrhea in Travelers: Response to Rifaximin Therapy. *Clinical Gastroenterology and Hepatology*. 2004; 2:135-138; and Steffen R, M.D., Sack D A, M.D., Riopel L, Ph.D., Zhi-Dong J, Ph.D., Sturchler M, M.D., Ericsson C D, M.D., Lowe B, M. Phil., Waiyaki P, Ph.D., White M, Ph.D., DuPont H L, M.D. Therapy of Travelers' Diarrhea With Rifaximin on Various Continents. *The American Journal of Gastroenterology*. May 2003, Volume 98, Number 5, all of which are incorporated herein by reference in their entirety.

Embodiments also provide pharmaceutical compositions comprising one or more of a Form ζ, Form η, Form α-dry, Form ι, Form β-1, Form β-2, Form ε-dry, mesylate Form or amorphous forms of rifaximin and a pharmaceutically acceptable carrier. That is, formulations may contain only one polymorph or may contain a mixture of more than one polymorph. Mixtures may be selected, for example on the basis of desired amounts of systemic adsorption, dissolution profile, desired location in the digestive tract to be treated, and the like. Embodiments of the pharmaceutical composition further comprise excipients, for example, one or more of a diluting agent, binding agent, lubricating agent, disintegrating agent, coloring agent, flavoring agent or sweetening agent. One composition may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In an embodiment, the rifaximin polymorph is administered to the subject using a pharmaceutically-acceptable formulation, e.g., a pharmaceutically-acceptable formulation that provides sustained delivery of the rifaximin polymorph to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those rifaximin polymorphs of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is preferably "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a rifaximin forms disclosed herein include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred %, this amount will range from about 1% to about ninety-nine % of active ingredient, preferably from about 5% to about 70%, most preferably from about 10% to about 30%.

Methods of preparing these compositions include the step of bringing into association a rifaximin polymorph(s) with the carrier and, optionally, one or more accessory ingredients. In general, the formulations are prepared by uniformly and intimately bringing into association a rifaximin polymorph with liquid carriers, or finely divided solid carriers, or both, and then, if necessary, shaping the product.

Compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a rifaximin polymorph(s) as an active ingredient. A compound may also be administered as a bolus, electuary or paste.

The amorphous form can be advantageously used in the production of medicinal preparations having antibiotic activity, containing rifaximin, for both oral and topical use. The medicinal preparations for oral use will contain rifaximin amorphous form together with the usual excipients, for example diluting agents such as mannitol, lactose and sorbitol; binding agents such as starches, gelatines, sugars, cellulose derivatives, natural gums and polyvinylpyrrolidone; lubricating agents such as talc, stearates, hydrogenated vegetable oils, polyethylenglycol and colloidal silicon dioxide; disintegrating agents such as starches, celluloses, alginates, gums and reticulated polymers; colouring, flavouring and sweetening agents.

Embodiments of the invention include solid preparations administrable by the oral route, for instance coated and uncoated tablets, of soft and hard gelatin capsules, sugar-coated pills, lozenges, wafer sheets, pellets and powders in sealed packets or other containers.

Medicinal preparations for topical use can contain rifaximin amorphous forms together with usual excipients, such as white petrolatum, white wax, lanoline and derivatives thereof, stearylic alcohol, propylene glycol, sodium lauryl sulfate, ethers of fatty polyoxyethylene alcohols, esters of fatty polyoxyethylene acids, sorbitan monostearate, glyceryl monostearate, propylene glycol monostearate, polyethylene glycols, methylcellulose, hydroxymethyl propylcellulose, sodium carboxymethylcellulose, colloidal aluminium and magnesium silicate, sodium alginate.

Embodiments of the invention relate to all of the topical preparations, for instance ointments, pomades, creams, gels and lotions.

In solid dosage forms of rifaximin for oral administration (capsules, tablets, pills, dragees, powders, granules and the like), the active ingredient is typically mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) colouring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the rifaximin polymorph(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active rifaximin polymorph(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions for rectal or vaginal administration may be presented as a suppository, which may be prepared by mixing one or more rifaximin polymorph(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams or spray formulations containing such carriers as are known in the art to be appropriate.

Dosage forms for the topical or transdermal administration of a rifaximin polymorph(s) include powders, sprays, ointments, pastes, creams, lotions, gels, solutions, patches and inhalants. The active rifaximin polymorph(s) may be mixed under sterile conditions with a pharmaceutically-acceptable carrier, and with any preservatives, buffers, or propellants which may be required.

Ointments, pastes, creams and gels may contain, in addition to rifaximin polymorph(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a rifaximin polymorph(s), excipients such as lactose, talc, silicic acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

The rifaximin polymorph(s) can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

An aqueous aerosol is made, for example, by formulating an aqueous solution or suspension of the agent together with conventional pharmaceutically-acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a rifaximin polymorph(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions suitable for parenteral administration may comprise one or more rifaximin polymorph(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, to prolong the effect of a drug, it is desirable to alter the absorption of the drug. This may be accomplished by the use of a liquid suspension of crystalline, salt oramorphous material having poor water solubility. The rate of absorption of the drug may then depend on its rate of dissolution which, in turn, may depend on crystal size and crystalline form. Alternatively, delayed absorption of a drug form is accomplished by dissolving or suspending the drug in an oil vehicle.

Injectable depot forms are made by forming microencapsule matrices of rifaximin polymorph(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the rifaximin polymorph(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the rifaximin polymorph(s), which may be used in a suitable hydrated form, and/or the pharmaceutical compositions of the present invention, are formulated into pharmaceutically-acceptable dosage forms by methods known to those of skill in the art.

Actual dosage levels and time course of administration of the active ingredients in the pharmaceutical compositions may be varied so as to obtain an amount of the active ingredient which is effective to achieve the desired therapeutic response for a particular subject, composition, and mode of administration, without being toxic to the subject. An exemplary dose range is from 25 to 3000 mg per day.

A preferred dose of the rifaximin polymorph for the present invention is the maximum that a subject can tolerate without developing serious side effects. Preferably, the rifaximin polymorph of the present invention is administered at a concentration of about 1 mg to about 200 mg per kilogram of body weight, about 10—about 100 mg/kg or about 40 mg—about 80 mg/kg of body weight. Ranges intermediate to the above-recited values are also intended to be part.

In combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the compound of this invention is less than its effective amount in case the other therapeutic agent is not administered. In another embodiment, the effective amount of the conventional agent is less than its effective amount in case the compound of this invention is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more therapies are administered within the same subject's visit.

In certain embodiments, one or more compounds and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the administration of the same compounds may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a rifaximin polymorph may be repeated and the administration may be separated by at least 1 day, 2 days, 3 days, 5 days, 10 days, 15 days, 30 days, 45 days, 2 months, 75 days, 3 months, or at least 6 months.

Certain indications may require longer treatment times. For example, travelers' diarrhea treatment may only last from between about 12 hours to about 72 hours, while a treatment for Crohn's disease may be from between about 1 day to about 3 months. A treatment for hepatic encephalopathy may be, for example, for the remainder of the subject's life span. A treatment for IBS may be intermittent for weeks or months at a time or for the remainder of the subject's life.

Article of Manufacture

Another embodiment includes articles of manufacture that comprise, for example, a container holding a pharmaceutical composition suitable for oral or topical administration of rifaximin in combination with printed labeling instructions providing a discussion of when a particular dosage form should be administered with food and when it should be taken on an empty stomach. Exemplary dosage forms and administration protocols are described infra. The composition will be contained in any suitable container capable of holding and dispensing the dosage form and which will not significantly interact with the composition and will further be in physical relation with the appropriate labeling. The labeling instructions will be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

Another aspect is an article of manufacture that comprises a container containing a pharmaceutical composition comprising rifaximin wherein the container holds preferably rifaximin composition in unit dosage form and is associated with printed labeling instructions advising of the differing absorption when the pharmaceutical composition is taken with and without food.

Packaged compositions are also provided, and may comprise a therapeutically effective amount of rifaximin. Rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

Kits are also provided herein, for example, kits for treating a bowel disorder in a subject. The kits may contain, for example, one or more of a Form ζ, Form η, Form α-dry, Form ι, Form β-1, Form β-2, Form ε-dry, mesylate Form or amorphous forms of rifaximin and instructions for use. The instructions for use may contain proscribing information, dosage information, storage information, and the like.

Packaged compositions are also provided, and may comprise a therapeutically effective amount of one or more of a polymorph of rifaximin and a pharmaceutically acceptable carrier or diluent, wherein the composition is formulated for treating a subject suffering from or susceptible to a bowel disorder, and packaged with instructions to treat a subject suffering from or susceptible to a bowel disorder.

EXAMPLES

Materials

Rifaximin was stored in a dessicator at ambient temperature.

Characterization of Forms

Some of the hydrated, salt and amorphous forms of rifaximin, were characterized by one or more of XRPD, thermal analysis, FT-IR, FT-Raman, $^{13}$C NMR. Dried materials obtained by vacuum drying or heating the hydrates were labeled "dry". These materials exhibited XRPD patterns that were shifted or contained one or two additional small peaks when compared to the undried material.

Amorphous Material

Amorphous rifaximin (FIG. 1) was prepared by milling Form γ or Forms γ+η at ambient temperature. Amorphous rifaximin was physically stable under various relative humidities and exhibited a high glass transition temperature onset of 199° C.

Figure 3:
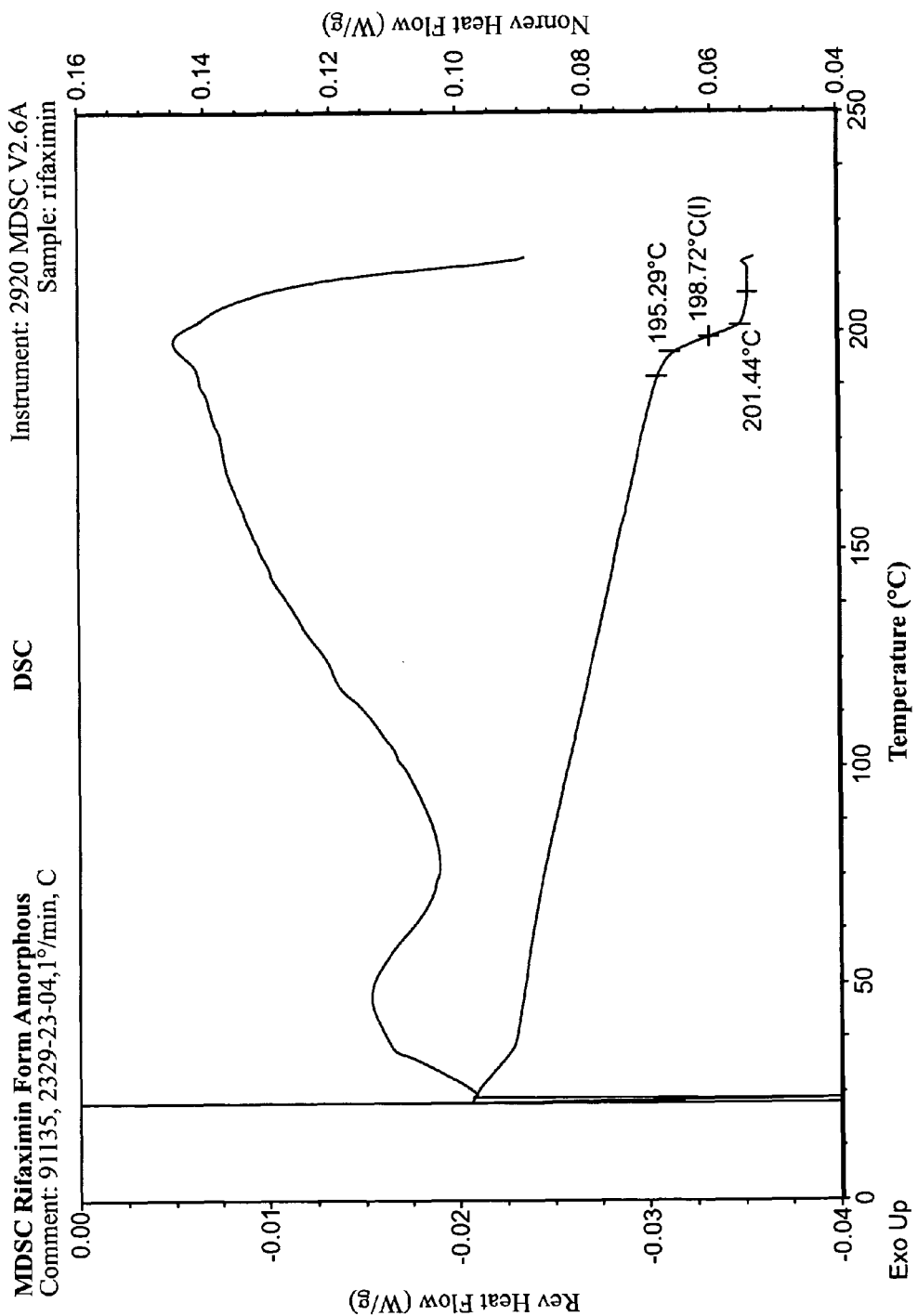
FIG. 3 shows an exemplary MDSC of rifaximin form amorphous.

TG analysis of amorphous rifaximin demonstrated a 1.5% weight loss to 100° C., accompanied by a broad endotherm at 78° C. in the DSC trace (FIG. 2), indicating the material contained residual solvent. A minor endotherm at 203° C. was also observed in the DSC trace. Cyclic DSC was performed to dry the sample and determine the $T_g$, however the glass transition temperature was not apparent from the data. Modulated differential scanning calorimetry showed the glass transition ($T_g$) temperature onset to be approximately 199° C. (FIG. 3). Amorphous rifaximin was hygroscopic gaining 11.6% weight under 95% RH. The gained weight was lost during the desorption cycle. The post moisture balance XRPD pattern was amorphous.

The behavior of amorphous rifaximin under various relative humidities was also investigated. Amorphous material was stored under 43% RH for 5 days, 58% RH for 8 days and 75% RH for 2 days. The material remained amorphous by XRPD analysis.

Crystallization of rifaximin was conducted using water and varying ethanol/water ratios using a variety of techniques as disclosed herein. Additionally, drying studies were performed as well as stressing under various relative humidities.

Amorphous rifaximin was characterized by cyclic DSC and TG analyses: crash precipitation from ethyl acetate with heptane, lyophilization in p-dioxane:water 1:1, and fast evaporation from acetone. The cyclic DSC thermograms did not show evidence of a glass transition. A standard DSC test was run on the amorphous sample generated by crash precipitation from ethyl acetate with heptane, and showed two broad endotherms at approximately 79 and 204° C., indicative of likely desolvation followed by decomposition. Analysis by modulated DSC is pending for this sample. All the amorphous samples showed weight loss ranging from approximately 5 to 6% from 25 to 200° C. by TG, indicating all three preparations likely contain residual solvent.

Two amorphous preparations of Rifaximin (one from lyophilization in p-dioxane:water 1:1, the other from crash precipitation in ethyl acetate with heptane, known as lyophilized amorphous rifaximin and crash amorphous rifaximin, respectively) were characterized by dynamic vapor sorption/desorption (DVS) analysis. Both samples were moderately hygroscopic, with a steady uptake of water (approximately 8% weight gain for both samples) from 5 to 95% relative humidity. DVS curves for both samples showed hysteresis, as both lost more weight/water on desorption than they had gained on adsorption. Crystallization was not observed by either post-DVS sample. Based on the data, relative humidity stressing studies of the two amorphous materials at 40° C./75% RH are recommended.

Vapor stressing experiments were done on amorphous material from two preparations: lyophilization from p-dioxane:water 1:1 and crash precipitation from ethyl acetate with heptane. After 6 days, one sample (stressed with toluene) appeared microscopically birefringent, indicative of crystallization, but showed no peaks by XRPD. The majority of the stressed samples appeared as clear red solutions after 6 days. Those solutions were placed in vials of antisolvent for vapor diffusion. Dry and wet milling experiments were conducted on amorphous materials from the two preparations mentioned above. Amorphous materials were recovered from the dry milling experiments.

Modulated DSC of x-ray amorphous rifaximin prepared from a crash precipitation experiment in ethyl acetate with heptane showed no evidence of a glass transition temperature. A second modulated DSC experiment on a sample of x-ray amorphous rifaximin from a vapor stress experiment with water is pending. The presence of water in the sample could possibly lower the glass transition temperature, potentially making it detectable by modulated DSC.

Crystallization of amorphous rifaximin to Form β was observed for vapor diffusion experiments in methanol and tetrahydrofuran, both utilizing water as an antisolvent.

TABLE 1

Amorphous Rifaximin

| Solvent | Conditions | Observation | XRPD Result |
|---|---|---|---|
| acetone | FE | red glass, not birefringent | amorphous, 2 halos |
| p-dioxane:H2O 1:1 | lyophilization | orange solids, not birefringent | amorphous, 2 halos |
| ethyl acetate | CP w/ heptane | bright orange, morphology unknown, not birefringent | amorphous, 2 halos |

TABLE 2

Characterization of Rifaximin, Amorphous Samples

| Technique | Analysis/Result |
|---|---|
| XRPD | amorphous, 2 halos |
| cycling DSC[a] | no $T_g$ observed |
| TG[b] | 5.39% from 25-200° C. |
| DVS[c] | 0.100% weight loss at 5% RH |
| | 8.364% eight gain from 5-95% RH |
| | 10.989% weight loss from 95-5% RH |
| XRPD | no peaks, possibly amorphous |
| XRPD | amorphous, 2 halos |
| DSC[a] | broad endo 79, broad endo 204 |
| cycling DSC[a] | no $T_g$ observed |
| modulated DSC[a] | no $T_g$ observed; broad endo 74 |
| TG[b] | 6.47% from 25-200° C. |
| DVS[d] | 1.606% weight loss at 5% RH |
| | 7.843% weight gain from 5-95% RH |
| | 9.172% weight loss from 95-5% RH |
| XRPD | no peaks, possibly amorphous |
| XRPD | amorphous, 2 halos |
| cycling DSC[a] | no $T_g$ observed |
| TG[b] | 4.52% from 25-200° C. |
| XRPD | amorphous |

[a]endo = endotherm, temperatures (° C.) reported are transition maxima. Temperatures are rounded to the nearest degree.
[b]weight loss (%) at a certain temperature; weight changes (%) are rounded to 2 decimal places; temperatures are rounded to the nearest degree.
[c]See 3436-54 for calculations.
[d]See 3436-55 for calculations.

TABLE 3

Stressing of Rifaximin, Amorphous Materials

| Solvent | Conditions | Observations | XRPD Result |
|---|---|---|---|
| DCM | VD w/ IPE, 11 days | red, glassy solid, not birefringent | amorphous |
| toluene | VS, RT, 6 days | red, spherulites of needles, birefringent | amorphous |
| water | VS, RT, 15 days | orange, aggregates and morphology unknown, not birefringent; dark read, agglomerate (very small amount), partially birefringent | amorphous |
| MEK | VD w/ IPE, 11 days | red, oily droplets in glassy solid, not birefringent | amorphous |

[a]Sample was analyzed by both Inel and Bruker XRPD to confirm result.

TABLE 4

Milling Experiments for Rifaximin, Amorphous Materials

| Amorphous Sample Source | Conditions | Observations | XRPD Result |
|---|---|---|---|
| lyophilization from p-dioxane:water 1:1 | 10 min. at 30 Hz, scraped sides, 10 min. at 30 Hz | bright orange, morphology unknown, not birefringent | amorphous |
| CP from EtOAc with heptane | 10 min. at 30 Hz, scraped sides, 10 min. at 30 Hz | bright orange, morphology unknown, not birefringent | amorphous |

TABLE 5

Characterization of Rifaximin Amorphous

| Analysis[a] | Conditions | Results |
|---|---|---|
| XRPD | Inel | amorphous |
| DSC | Method A (25-250-10) crimped pan | endotherm (major broad) 78° C. endotherm (minor) 203° C. |
| DSC MDSC | Cyclic DSC | Glass transition not determined Tg (glass transition) 199° C. |
| TGA | Method A (00-350-10) | 1.5% from 21° C. to 100° C. |
| MB | — | 0.7% wt loss upon equilibration at 5% RH 11.6% wt gain from 5 to 95% RH 11.3% wt loss from 95 to 5% RH ntbk ref. 2329-50 |
| Post-MB XRPD | Inel | amorphous |
| FT-IR | 100% API, 256 scans | conforms to structure |
| FT-Raman | 100% API, 256 scans | conforms to structure |

[a] XRPD = X-ray powder diffraction; DSC = differential scanning calorimetry; TGA = thermogravimetric analysis; MB = automated moisture sorption/desorption; FT-IR = Fourier transform infrared spectroscopy; $^1$H-NMR = solutions proton nuclear magnetic spectroscopy; $^{13}$C-ssNMR = carbon-13 solid state nuclear magnetic spectroscopy.

TABLE 6

Post-Moisture Sorption/Desorption Analysis

| Initial Form | Final Form |
|---|---|
| α dry | α dry |
| Amorphous | amorphous |

[a] XRPD results are from post moisture sorption/desorption analysis - sorption from 5% RH to 95% RH; desorption from 95% RH to 5% RH.

TABLE 7

Form amorphous

| Initial Form | Conditions | Final Form |
|---|---|---|
| Amorphous | Post MB | amorphous |
| Amorphous | 43% RH, 5 days | amorphous |
| Amorphous | 58% RH, 5 days | amorphous |
| Amorphous | 75% RH, 5 days | amorphous |
| γ | ground at 30 Hz, 10 min (5 minute intervals × 2) | amorphous |
| γ | ground at 30 Hz, 30 min (15 minute intervals × 2) | amorphous |
| γ + η | ground at 30 Hz, 45 min (15 minute intervals × 3) | amorphous |

TABLE 8

Stressing Under Various Relative Humidities

| Initial Form | Conditions[a] | Observations | XRPD Form |
|---|---|---|---|
| amorphous | 43% RH, 5 days | orange; small irregular particles; no B&E | amorphous |
| amorphous | 58% RH, 5 days | orange; small irregular particles; mostly no B&E | amorphous |
| amorphous | 75% RH, 5 days | orange; small irregular particles; mostly no B&E | amorphous |

[a] All samples stored at room temperature unless otherwise indicated; RH = relative humidity
[b] B = birefringence; E = extinction Materials Samples were stored in a dessicator. Solvents and other reagents used were purchased from commercial suppliers and used as received. Solvents were either HPLC or ACS grade.

Slow Evaporation (SE)

Solvent was added to weighed amounts of rifaximin in vials. Mixtures were sonicated to achieve complete dissolution of solids. The solutions were then filtered into clean vials. Solvents were slowly evaporated at ambient conditions.

Crash Cool (CC)

A sample of rifaximin in ethanol/water 1/0.45 was prepared and passed through 0.2-μm nylon filter into a clean vial. The vial containing the solution was then rapidly cooled by submersion in an ice bath for several seconds. Solids that precipitate were collected by filtration and dried.

Slurry Experiments

Test solvents were added to rifaximin in vials such that excess undissolved solids were present in solutions. The mixtures were than slurried on a shaker block or rotating wheel at subambient or room temperature.

Stressing Under Various Relative Humidities (RH)

A vial containing rifaximin was placed uncovered within a jar containing phosphorous pentoxide (P2O5) or a saturated salt solution in water. The jar was sealed and stored at either ambient temperature or in an oven at elevated temperature.

Slow Cool (SC)

Saturated solutions of rifaximin were prepared by slurrying excess solids in the test solvent at elevated temperature. The saturated solution was filtered while warm into a clean vial. The sample was allowed to cool to room temperature, and then further cooled to sub-ambient temperature using a refrigerator, followed by a freezer.

Milling

A solid sample of rifaximin was charged to a milling container with a milling ball. Samples were milled for 5 or 15 minute intervals (2×5 minutes, 2×15 minutes, and 3×15 minutes) at 30 Hz using a Retsch MM200 mixer mill. Solids were scraped from the sides of the vial after each interval.

Instrumental Techniques

X-ray Powder Diffraction (XRPD)

Shimadzu

X-ray powder diffraction (XRPD) analyses were performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5 to 40° 2θ was used. A silicon standard was analyzed to check the instrument alignment.

Data were collected and analyzed using XRD-6100/7000 v. 5.0. Samples were prepared for analysis by placing them in a sample holder.

Inel

X-ray powder diffraction (XRPD) analyses were performed using an Inel XRG-3000 diffractometer equipped with a CPS (Curved Position Sensitive) detector with a 2θ range of 120°. Real time data were collected using Cu-Kα radiation starting at approximately 4° 2θ at a resolution of 0.03° 2θ. The tube voltage and amperage were set to 40 kV and 30 mA, respectively. The monochromator slit was set at 5 mm by 160 μm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 300 sec. Instrument calibration was performed using a silicon reference standard.

Variable Temperature XRPD (VT-XRPD)

Variable-temperature XRPD (VT-XRPD) was performed on a Shimadzu XRD-6000 X-ray powder diffractometer equipped with an Anton Paar HTK 1200 high temperature stage. The sample was packed in a ceramic holder and analyzed from 2.5 to 40° 2θ at 3°/min (0.4 sec/0.02° step). The heating rate was 10° C./min. A silicon standard was analyzed to check the instrument alignment. Temperature calibration was performed using vanillin and sulfapyridine standards. Data were collected and analyzed using XRD-6000 v. 4.1.

Variable Relative Humidity XRPD (VRH-XRPD)

VRH-XRPD was performed on a Shimadzu XRD-6000 X-ray powder diffractometer equipped with a relative humidity generator, RH-200. This analysis is non-cGMP. The sample was packed in a ceramic holder and analyzed from 2.5-40° 2θ at 3°/min (0.4 sec/0.02° step) at approximately 32° C. The RH profile for the chamber is specified in the tables. XRPD patterns were collected during this time frame every 15 minutes for two hours. A data logger (SN#05012010) was used to measure the relative humidity in the chamber (see DATA section pages 57-60). A silicon standard was analyzed to check the XRPD instrument alignment. XRPD Data were collected and analyzed using XRD-6100/7000 v.5.0.

Reference XRPD Patterns

Reference XRPD patterns were obtained from US or European Patents or Patent Applications and converted to electronic files using UN-SCAN-IT version 6.0 (non-cGMP).

Optical Microscopy

Optical microscopy was performed using a Leica MZ12.5 stereomicroscope. Various objectives typically ranging from 0.8-4× were used with crossed-polarized light to view samples. Samples were viewed in situ.

Thermal Analyses

Differential Scanning Calorimetry (DSC)

Differential scanning calorimetry (DSC) was performed using a TA Instruments differential scanning calorimeter 2920. The sample was placed into an aluminum DSC pan, and the weight accurately recorded. The pan was covered with a lid and then crimped or left uncrimped. The sample cell was equilibrated at 25° C. and heated under a nitrogen purge at a rate of 10° C./min, up to a final temperature of 250 or 350° C. Indium metal was used as the calibration standard. Reported temperatures are at the transition maxima.

Method A: 25-250-10: initial equilibration at 25° C., heated to 250° C. at 10° C./min Method B: 25-350-10: initial equilibration at 25° C., heated to 350° C. at 10° C./min Cyclic Differential Scanning Calorimetry Cyclic DSC was performed using a TA Instruments 2920 differential scanning calorimeter. The sample was placed into a hermetically sealed DSC pan, and the weight accurately recorded. The pan was covered with a lid containing a laser pinhole. The method was as follows:
1. Equilibrate at −50° C.
2. Ramp 20° C./min to 80° C.
3. Isothermal at 80° C. for 1 min
4. Equilibrate at −50° C.
5. Ramp 20° C./min to 220° C.

Indium metal was used as the calibration standard. Reported temperature is at the transition maxima.

Modulated Differential Scanning Calorimetry (MDSC)

Modulated differential scanning calorimetry (MDSC) data were obtained on a TA Instruments differential scanning calorimeter 2920 equipped with a refrigerated cooling system (RCS). The sample was placed into an aluminum DSC pan, and the weight accurately recorded. The pan was covered with a lid perforated with a laser pinhole to allow for pressure release, and then hermetically sealed. MDSC data were obtained using a modulation amplitude of +/−0.8° C. and a 60 second period with an underlying heating rate of 1° C./min from 25-225° C. The temperature and the heat capacity were calibrated using indium metal and sapphire as the calibration standards, respectively. The reported glass transition temperatures are obtained from the half-height/inflection of the step change in the reversible heat flow versus temperature curve.

Thermogravimetric (TG) Analyses

Thermogravimetric (TG) analyses were performed using a TA Instruments 2950 thermogravimetric analyzer. Each sample was placed in an aluminum sample pan and inserted into the TG furnace. The furnace was first equilibrated at 25° C. or started directly from ambient temperature, then heated under nitrogen at a rate of 10° C./min, up to a final temperature of 350° C. Nickel and Alumel™ were used as the calibration standards. Methods for specific samples are referred to as summarized below Method A: 00-350-10: no initial equilibration; analysis started directly from ambient, sample heated to 350° C. at 10° C./min Method B: 25-350-10: initial equilibration at 25° C., sample heated to 350° C. at 10° C./min Method C: 00-300-10: no initial equilibration; analysis started directly from ambient, sample heated to 300° C. at 10° C./min Spectroscopy Fourier Transform Infrared (FT-IR)

The IR spectra were acquired on a Magna-IR 860® Fourier transform infrared (FT-IR) spectrophotometer (Thermo Nicolet) equipped with an Ever-Glo mid/far IR source, an extended range potassium bromide (KBr) beamsplitter, and a deuterated triglycine sulfate (DTGS) detector. An attenuated total reflectance (ATR) accessory (the Thunderdome™, Thermo Spectra-Tech), with a germanium (Ge) crystal was used for data acquisition. The spectra represent 256 co-added scans collected at a spectral resolution of 4 cm$^{-1}$. A background data set was acquired with a clean Ge crystal. A Log 1/R(R=reflectance) spectrum was acquired by taking a ratio of these two data sets against each other. Wavelength calibration was performed using polystyrene.

Fourier Transform Raman (FT-Raman)

FT-Raman spectra were acquired on a Raman accessory module interfaced to a Magna 860® Fourier transform infrared (FT-IR) spectrophotometer (Thermo Nicolet). This module uses an excitation wavelength of 1064 nm and an indium gallium arsenide (InGaAs) detector. Approximately 0.6-2.0 W of Nd:YVO$_4$ laser power was used to irradiate the sample. The samples were prepared for analysis by placing the material in a glass tube and positioning the tube in a gold-coated tube holder in the accessory A total of 256 or 1024 sample scans were collected from 98-3600 cm$^{-1}$ at a spectral resolution of 4 cm$^{-1}$, using Happ-Genzel apodization. Wavelength calibration was performed using sulfur and cyclohexane.

Automated Moisture Sorption/Desorption

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

Solid State $^{13}$C Nuclear Magnetic Resonance (NMR)

Samples were prepared for solid-state NMR spectroscopy by packing them into 4 mm PENCIL type zirconia rotors. The specific acquisition parameters are listed on the plot of the first full spectrum of each sample in the data section.

XRPD Data for Rifaximin Forms

High resolution XRPD data were collected on rifaximin forms ζ and η to identify peak positions as well as aid in indexing the patterns. Form ζ was successfully indexed using this data. Due to the disorder inherent in Form η attempts to index the XRPD pattern were unsuccessful. The XRPD peak list for rifaximin Form ζ was generated using the results of the indexed pattern. XRPD peak lists for rifaximin Form η and X-ray amorphous were generated using PatternMatch, an SSCI software package. The diffractograms were compared to the software generated peak list to ensure peaks selected were real. Broad and/or low intensity peaks as well as peaks beyond 20° 2 θ were not included in the peak position tables.

Preparation Methods for Select Rifaximin Forms

Rifaximin X-Ray Amorphous

Figure 4:
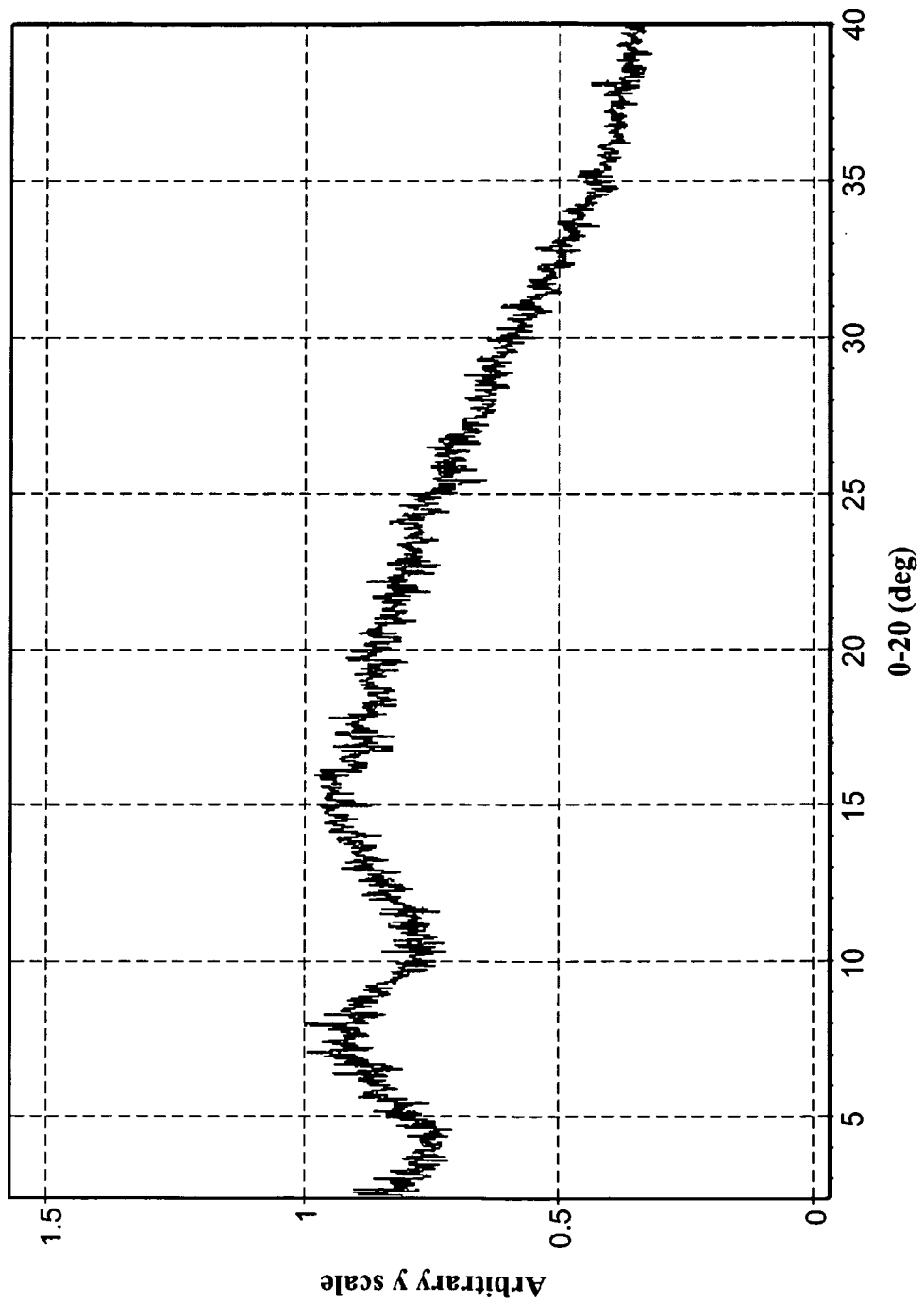
FIG. 4 depicts an exemplary XRPD pattern of rifaximin form amorphous.
Figure 5:
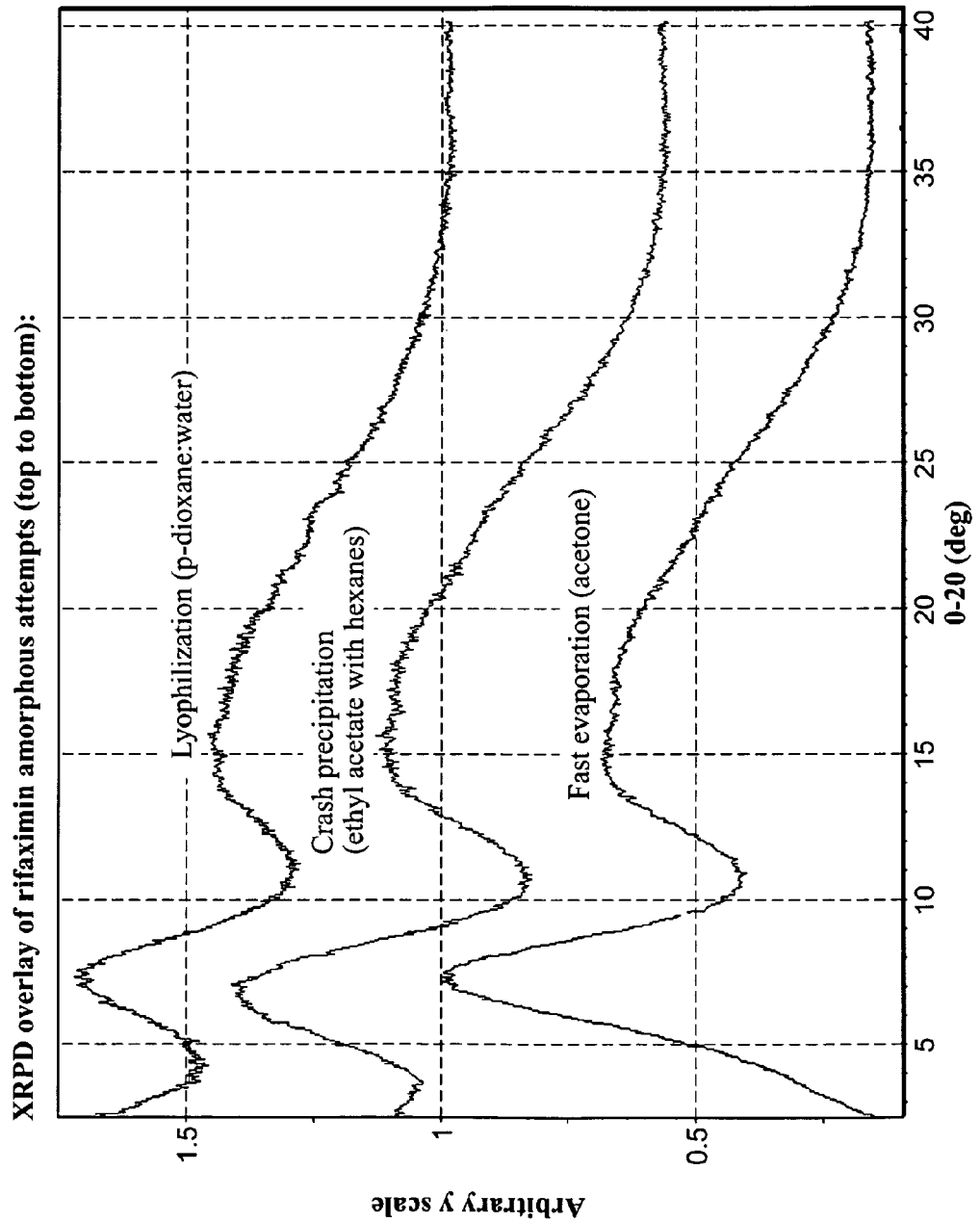
FIG. 5 depicts an exemplary XRPD overlay of rifaximin amorphous attempts.
Figure 6:
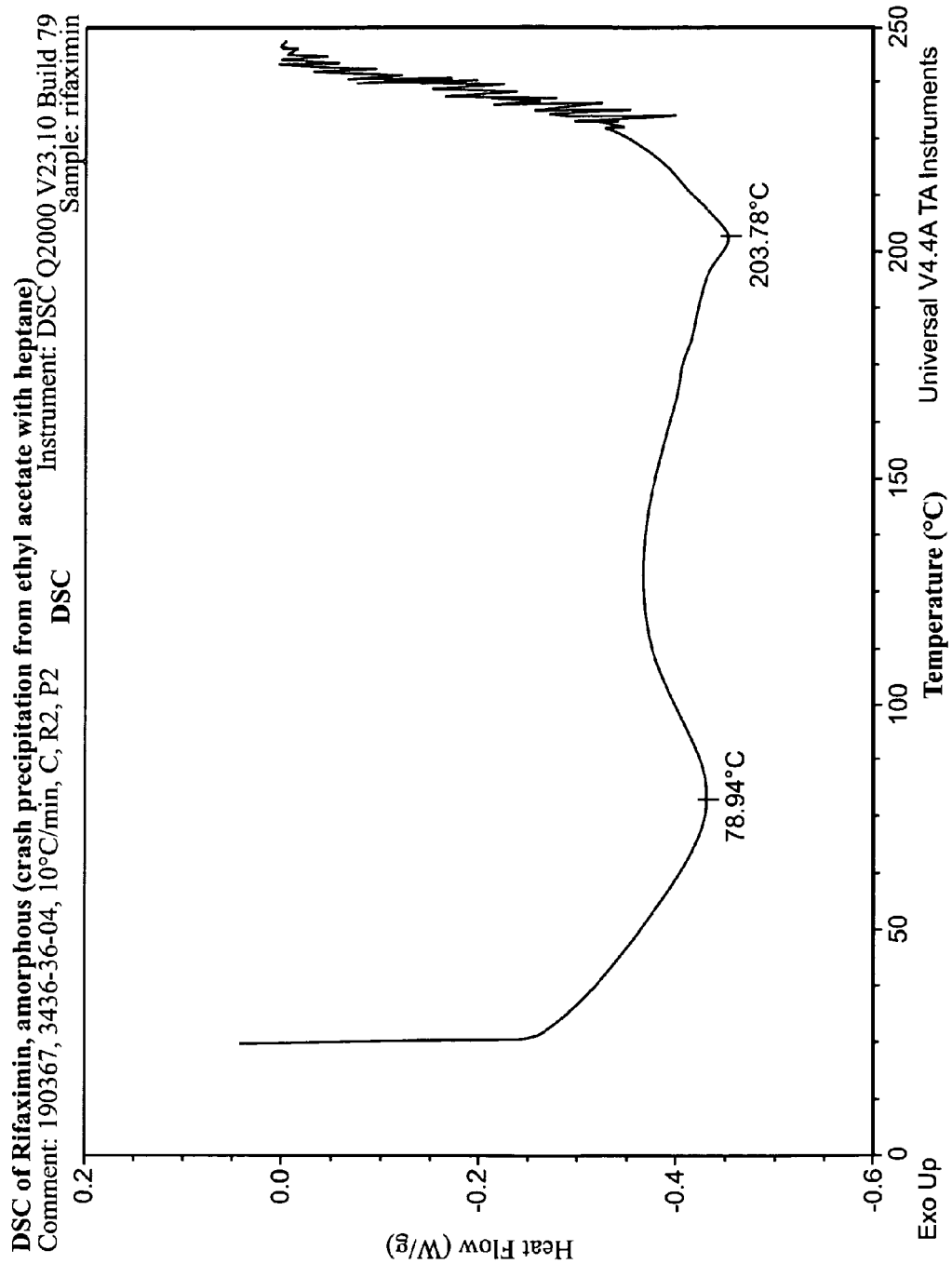
FIG. 6 depicts an exemplary DSC of rifaximin, amorphous (crash precipitation from ethyl acetate with heptane).
Figure 7:
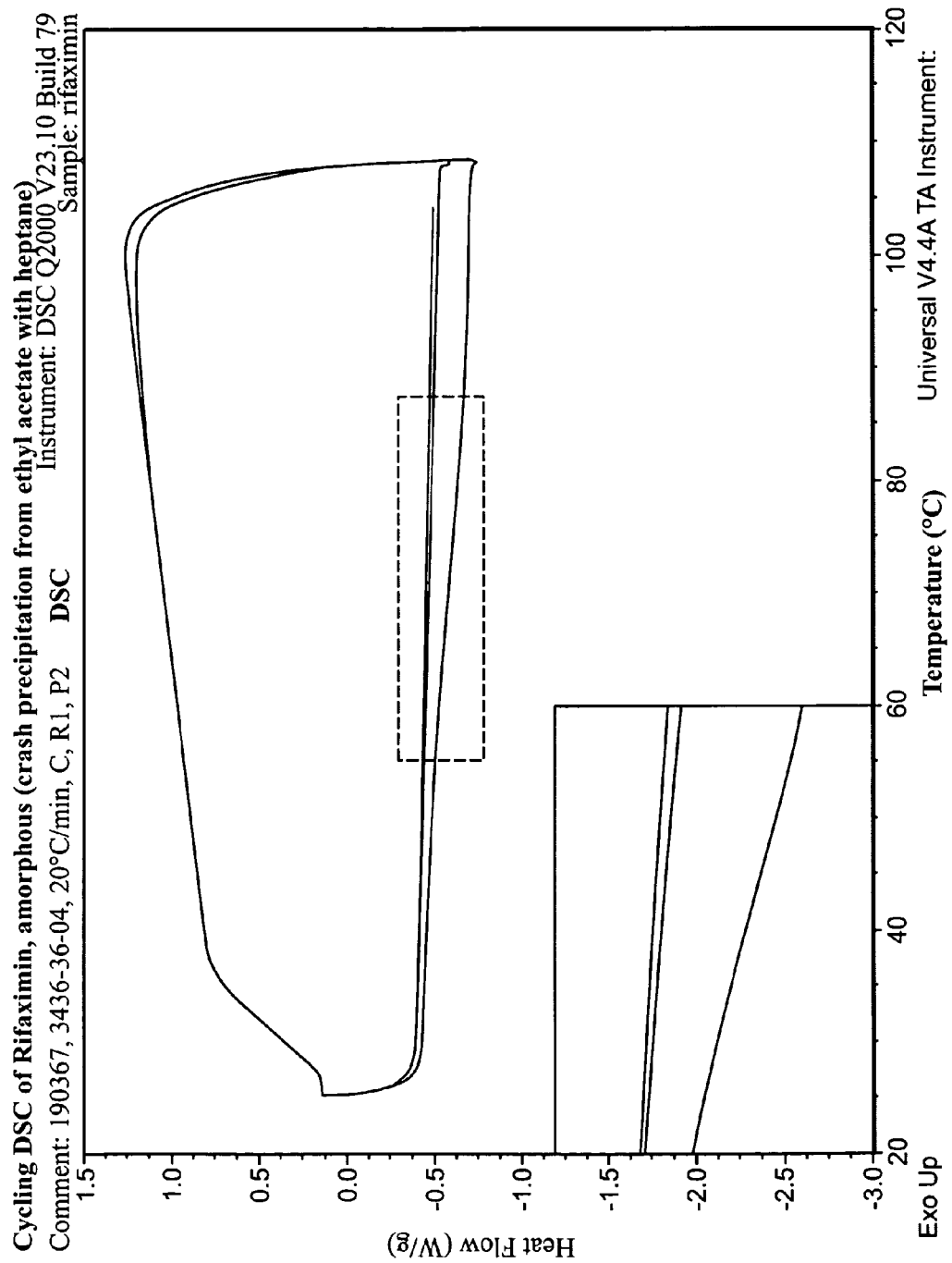
FIG. 7 depicts exemplary results of cycling DSC of rifaximin, amorphous (crash precipitation from ethyl acetate with heptane).
Figure 8:
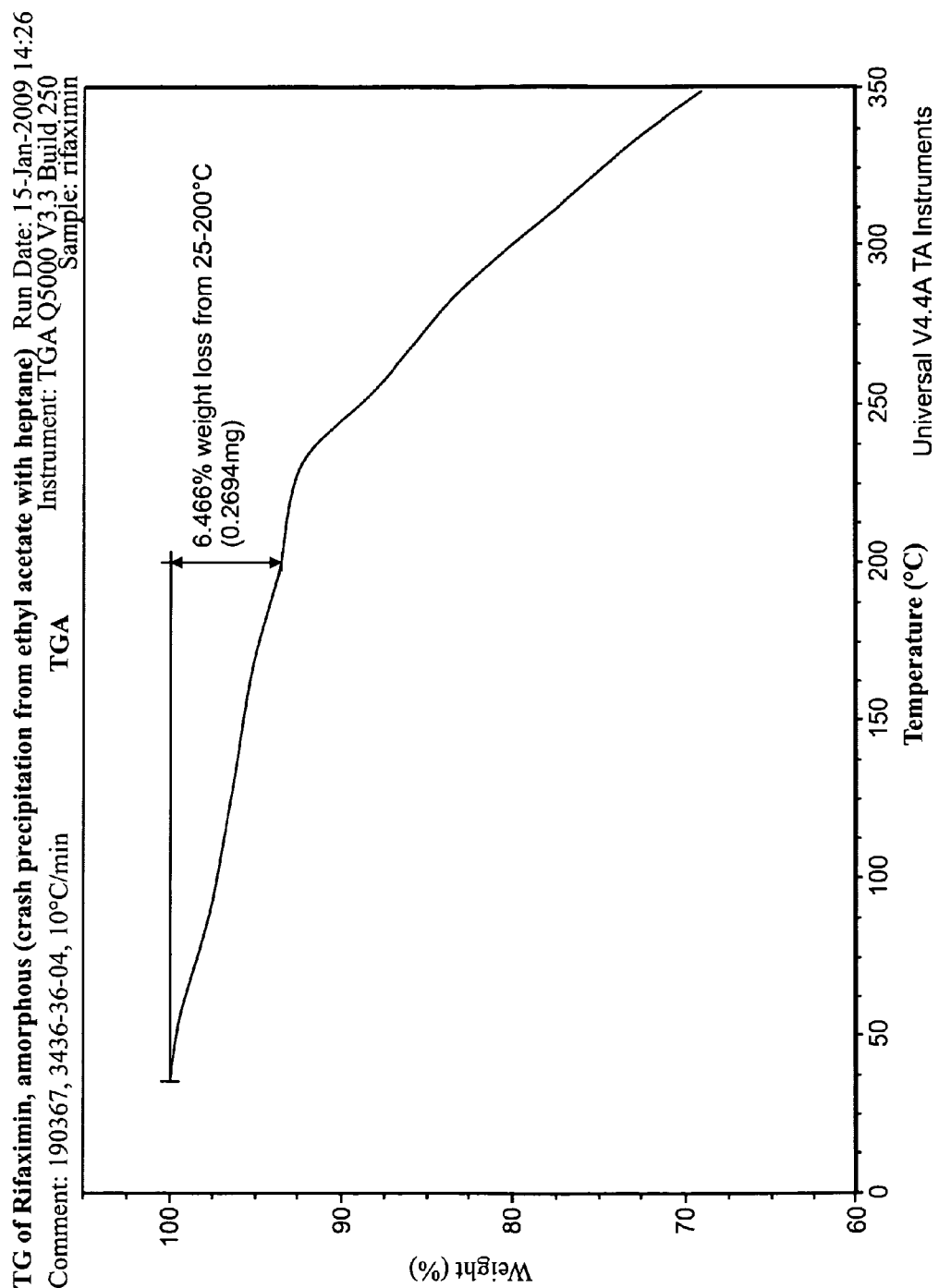
FIG. 8 depicts exemplary results of TG of rifaximin, amorphous (crash precipitation from ethyl acetate with heptane).
Figure 9:
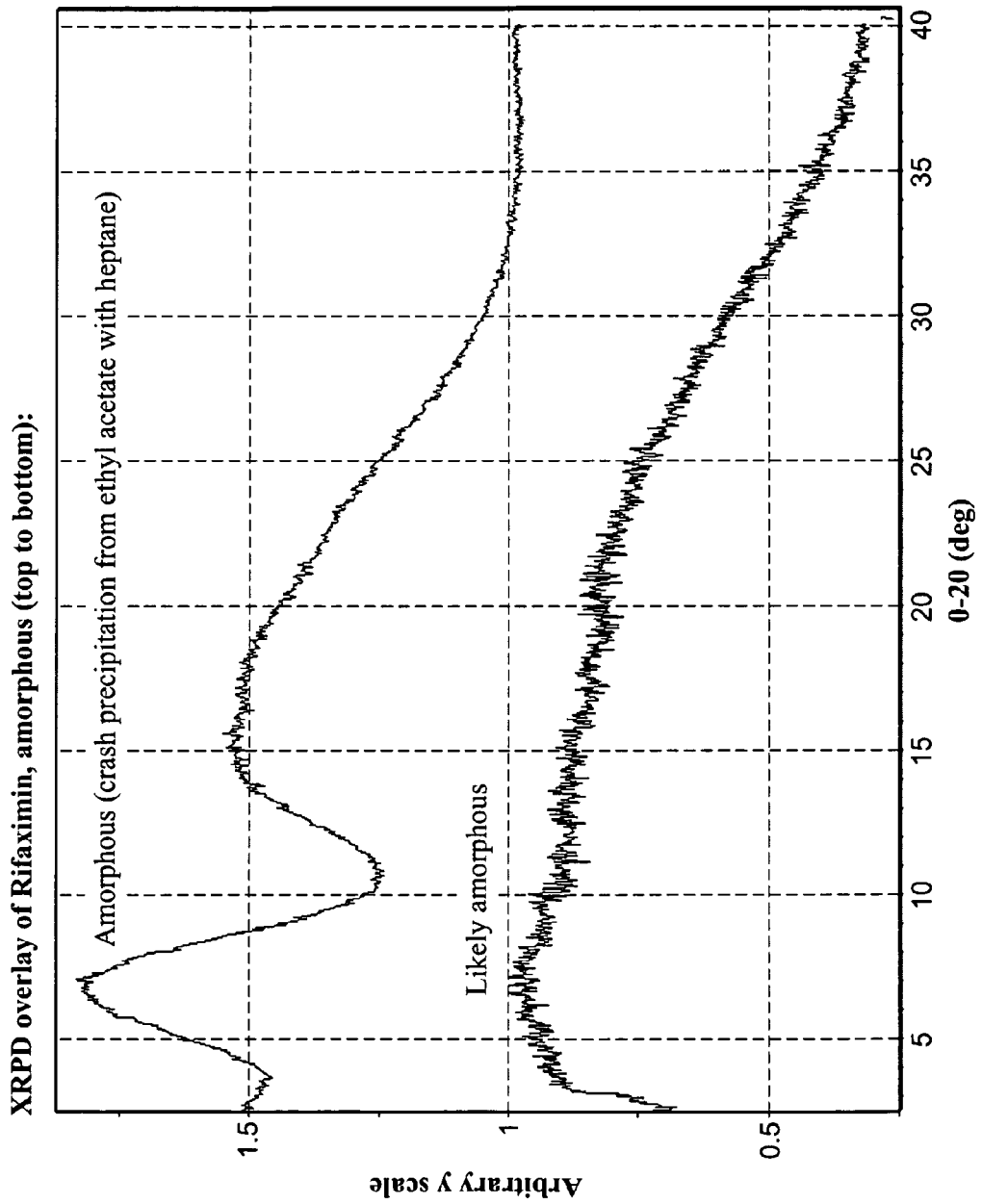
FIG. 9 depicts an exemplary XRPD overlay of rifaximin, amorphous (top to bottom): amorphous (crash precipitation from ethyl acetate with heptane) and likely amorphous.
Figure 10:
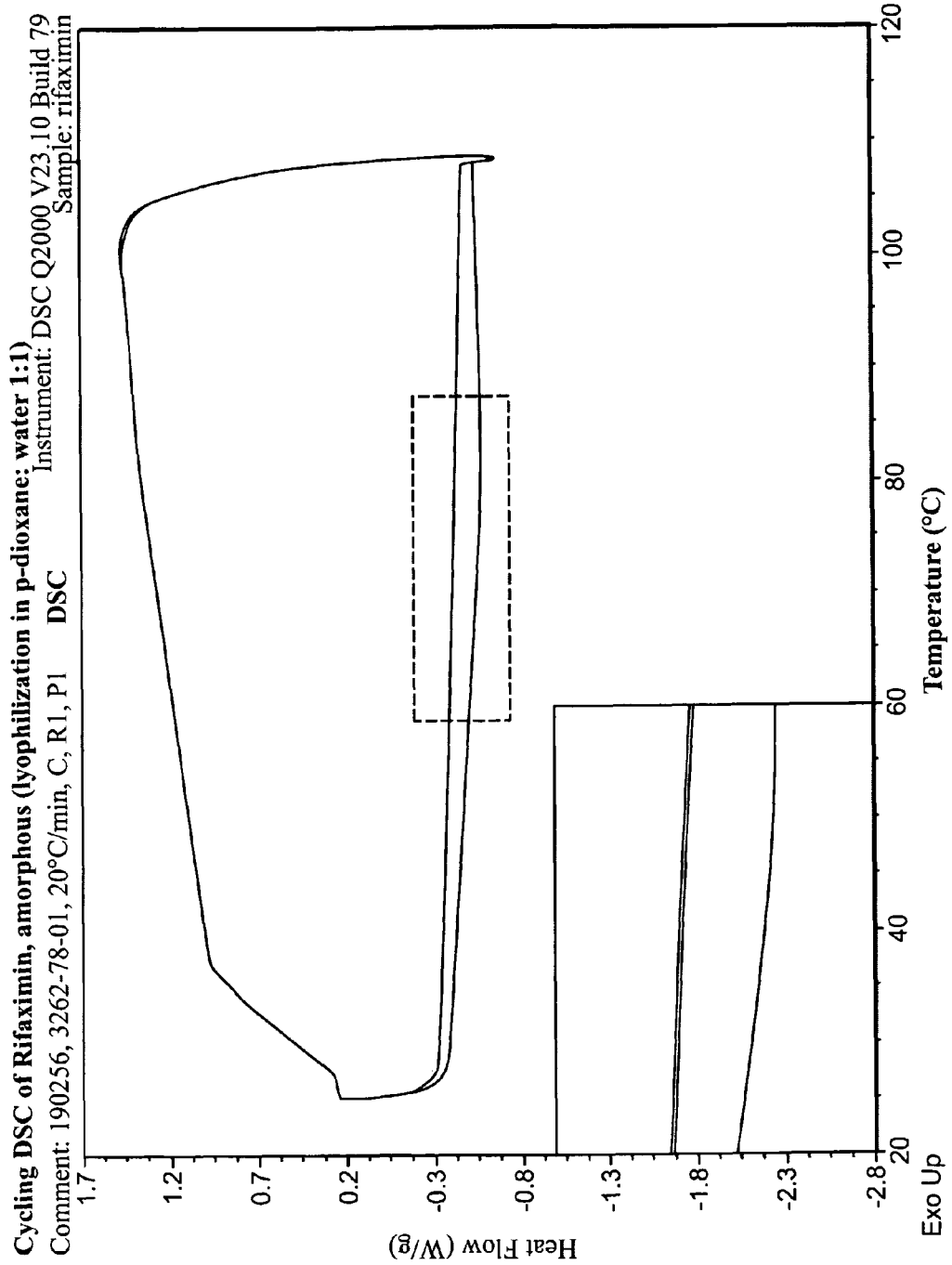
FIG. 10 depicts exemplary results of cycling DSC of rifaximin, amorphous (lyophilization in p-dioxane:water 1:1).
Figure 11:
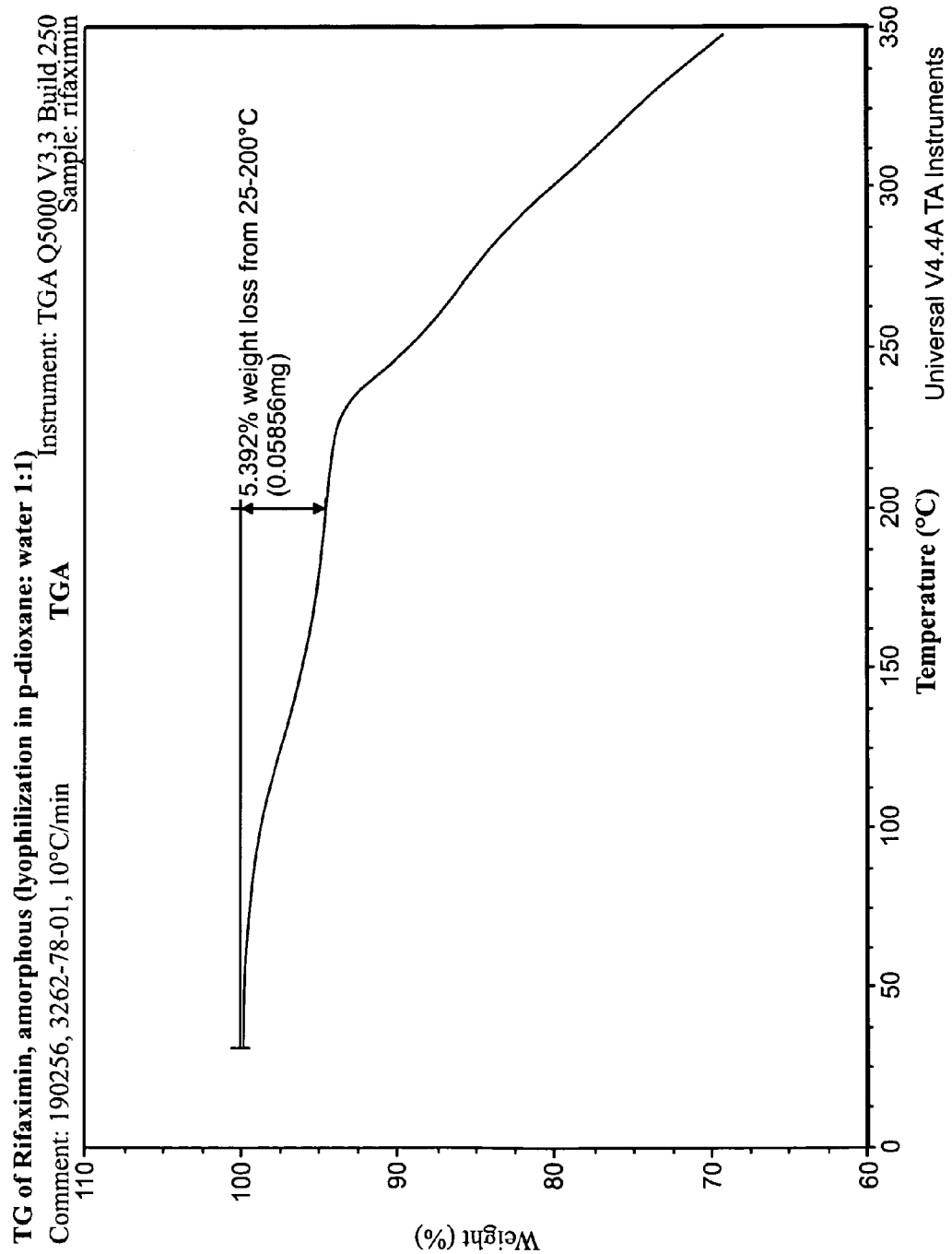
FIG. 11 depicts an exemplary results of TG of rifaximin, amorphous (lyophilization in p-dioxane:water 1:1).
Figure 12:
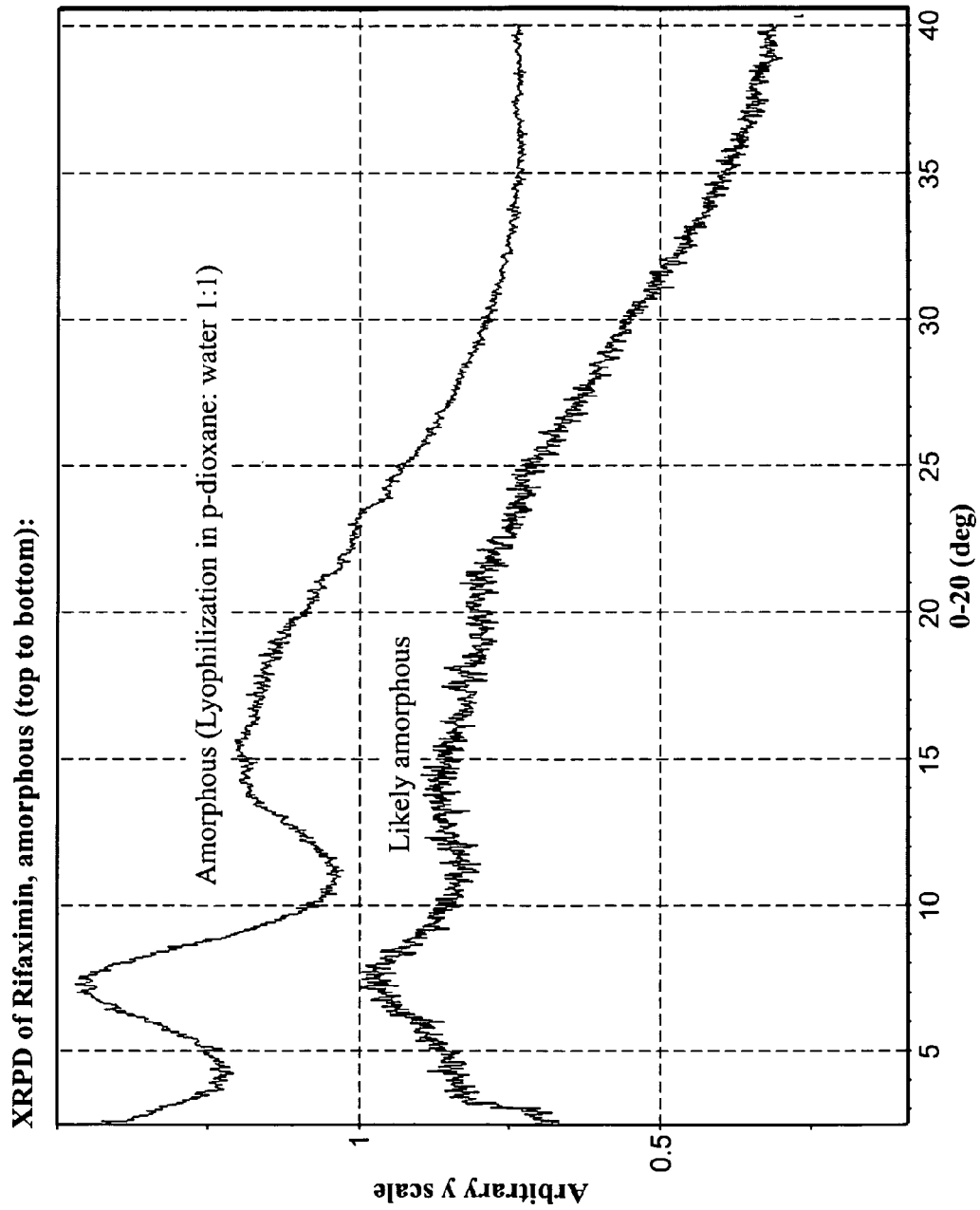
FIG. 12 depicts an exemplary XRPD of Rifaximin, amorphous (top to bottom): amorphous (lyophilization in p-dioxane:water 1:1) and likely amorphous.
Figure 13:
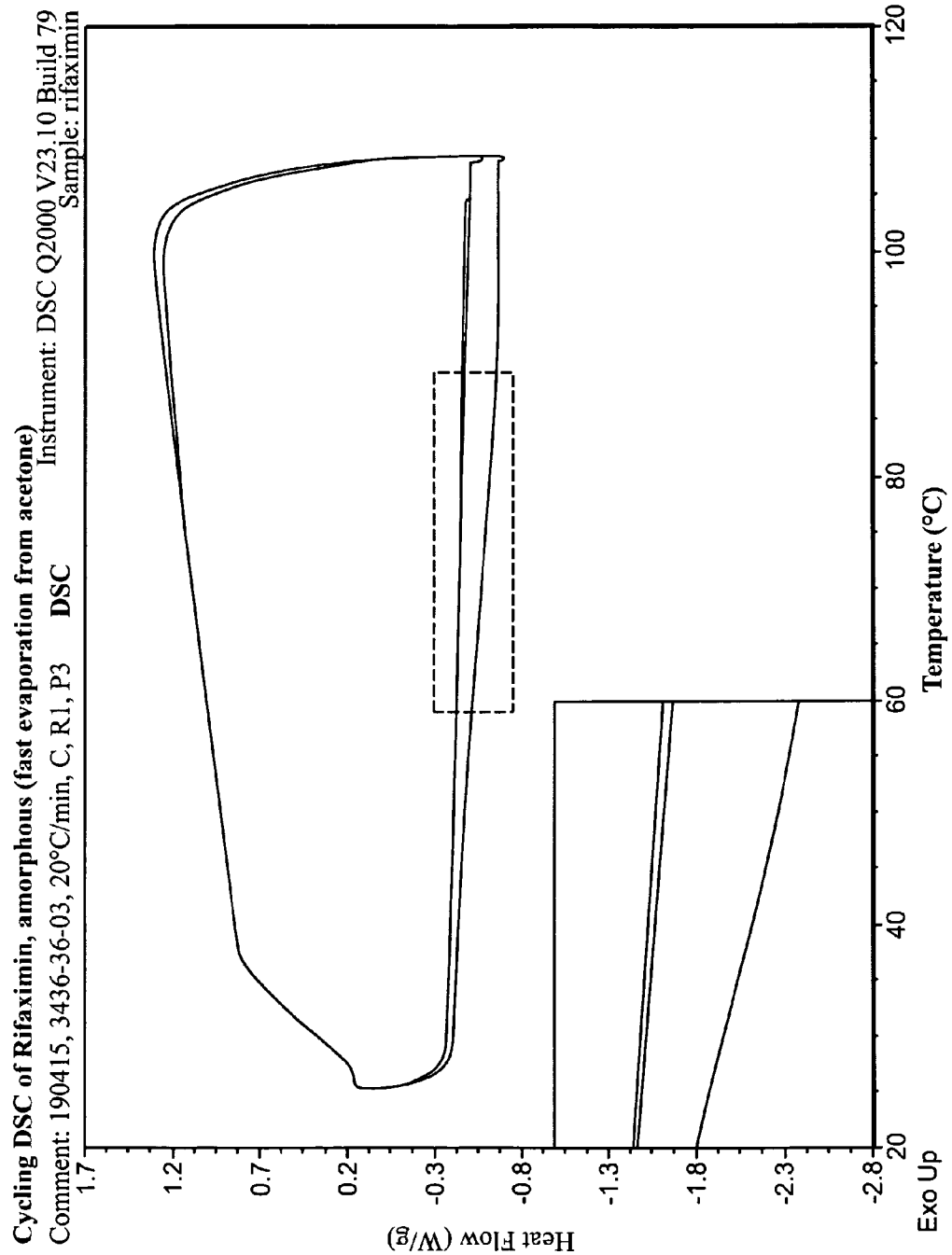
FIG. 13 depicts exemplary results of cycling DSC of rifaximin, amorphous (fast evaporation from acetone).
Figure 14:
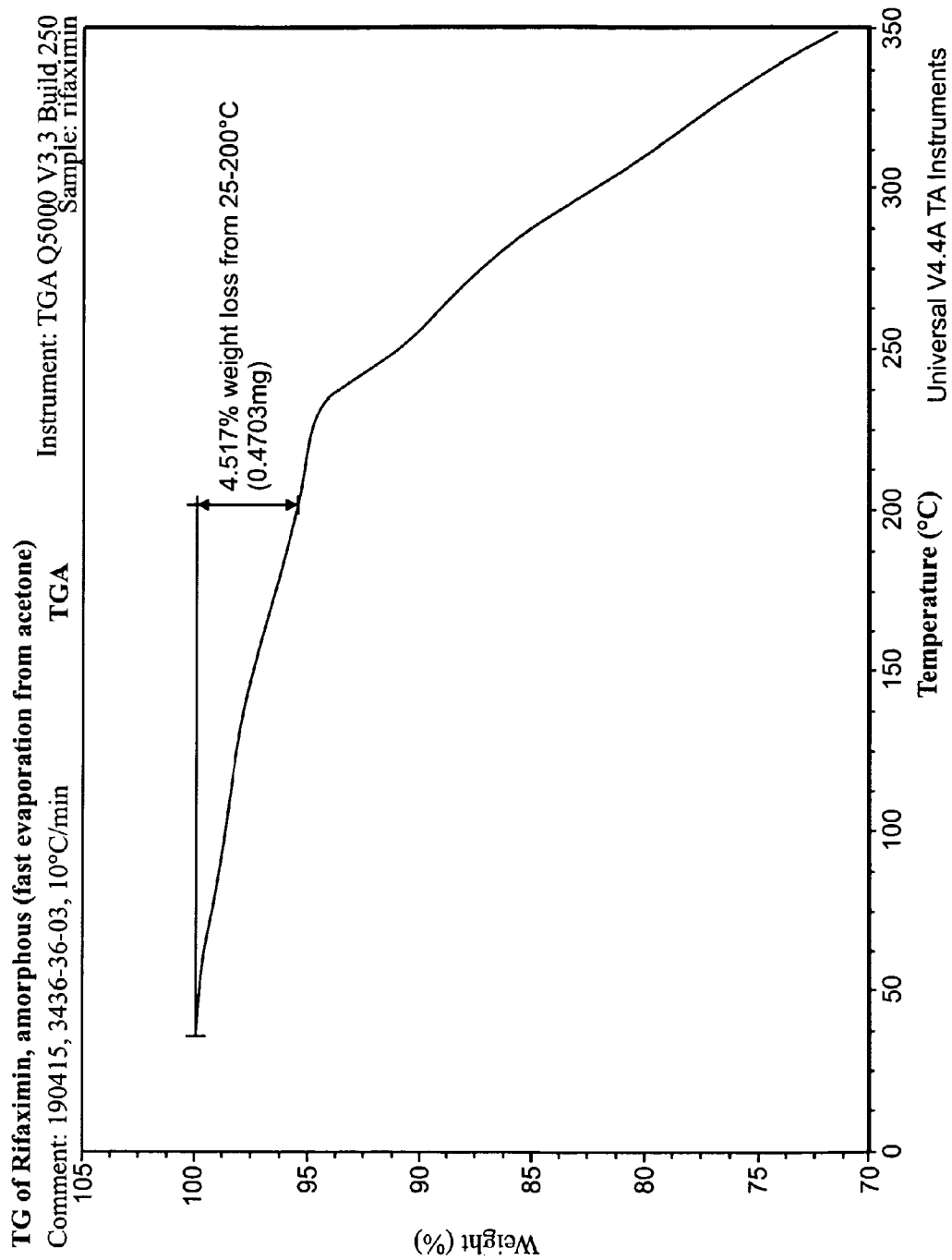
FIG. 14 depicts exemplary results of TG of rifaximin, amorphous (fast evaporation from acetone).
Figure 15:
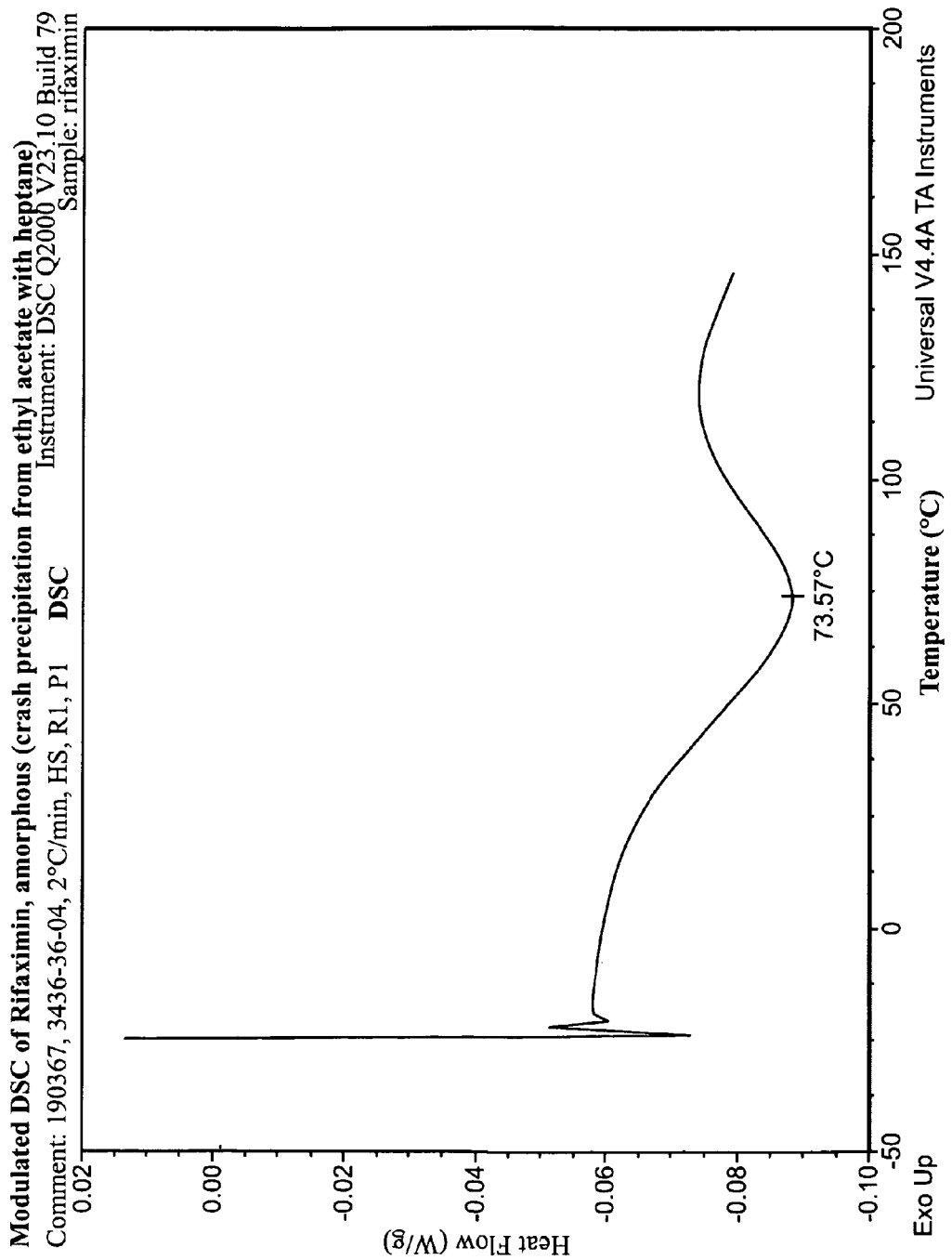
FIG. 15 depicts exemplary results of modulated DSC of rifaximin, amorphous (crash precipitation from ethyl acetate with heptane).
Figure 16:
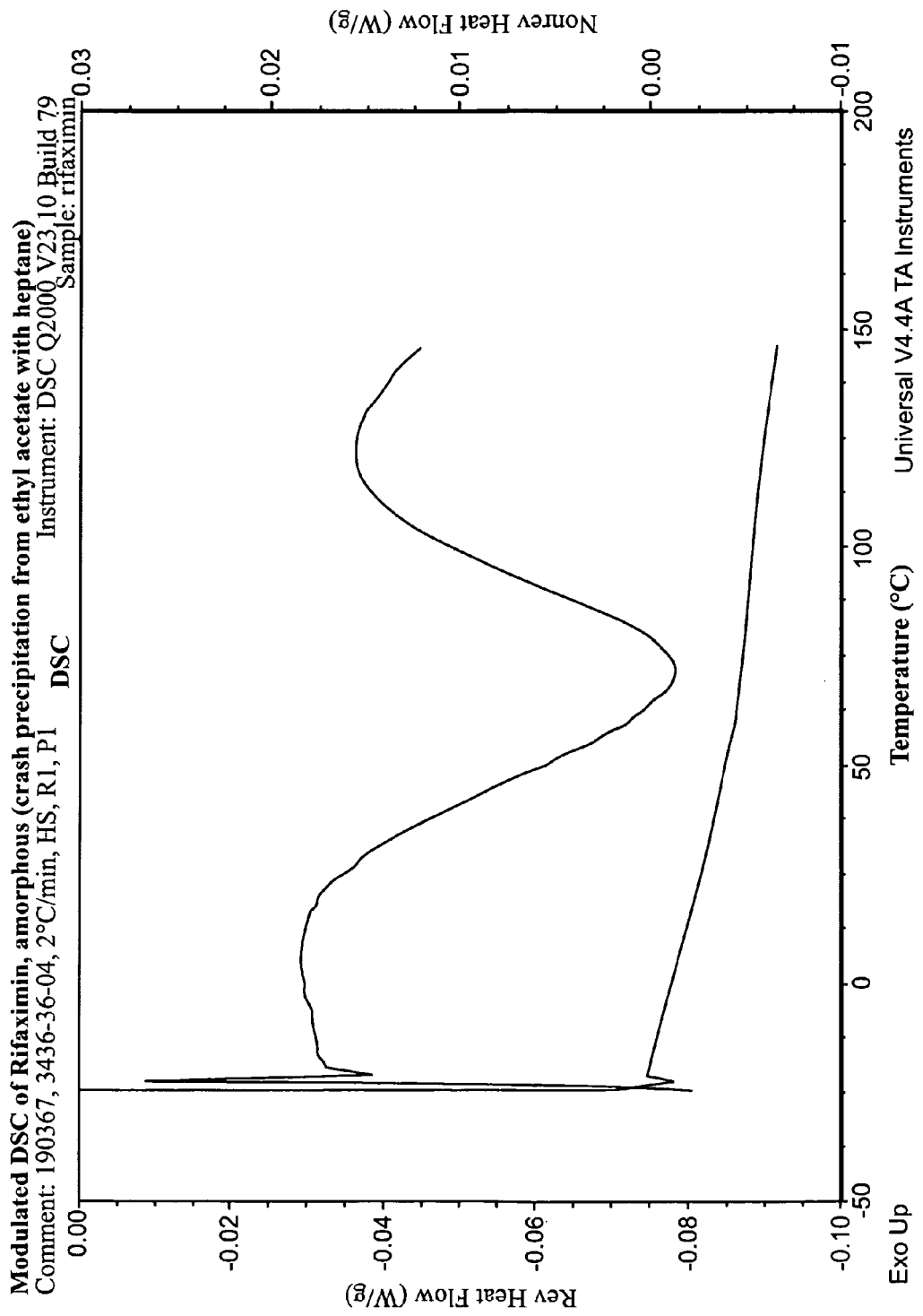
FIG. 16 depicts exemplary results of modulated DSC of rifaximin, amorphous (crash precipitation from ethyl acetate with heptane).

Rifaximin (50 mg, Form γ+η) was ground for three 15 minute cycles in a grinding jar at 30 Hz (total 45 minutes). Solids were scraped from sides of the jar after each cycle. Orange fragments were recovered and stored refrigerated, in a dessicator prior to analysis. (FIG. 4).

X-Ray Powder Diffraction (XRPD)

Inel XRG-3000 Diffractometer

X-ray powder diffraction (XRPD) analyses were performed using an Inel XRG-3000 diffractometer equipped with a CPS (Curved Position Sensitive) detector with a 2θ range of 120°. Real time data were collected using Cu-K α radiation. The tube voltage and amperage were set to 40 kV and 30 mA, respectively. The monochromator slit was set at 1-5 mm by 160 μm. The patterns are displayed from 2.5-40° 2 θ. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard.

PANalytical X'Pert Pro Diffractometer

Samples were also analyzed using a PANalytical X'Pert Pro diffractometer. The specimen was analyzed using Cu radiation produced using an Optix long fine-focus source. An elliptically graded multilayer minor was used to focus the Cu K α X-rays of the source through the specimen and onto the detector. The specimen was sandwiched between 3-micron thick films, analyzed in transmission geometry, and rotated to optimize orientation statistics. A beam-stop and a helium purge were used to minimize the background generated by air scattering. Soller slits were used for the incident and diffracted beams to minimize axial divergence. Diffraction patterns were collected using a scanning position-sensitive detector (X'Celerator) located 240 mm from the specimen. The data-acquisition parameters of each diffraction pattern are displayed above the image of each pattern in appendix data section. Prior to the analysis a silicon specimen (NIST standard reference material 640c) was analyzed to verify the position of the silicon 111 peak.

TABLE 9

XRPD Range of Amorphous halo of Rifaximin Form X-ray Amorphous Position (°2θ)

5.1-10.1 (amorphous halo range)
7.3 (approximate halo maximum)
11.3-17.8 (amorphous halo range)
15.8 (approximate halo maximum)

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A process for producing an amorphous form of rifaximin comprising grinding Form γ of rifaximin or a mixture of Form γ and Form η of rifaximin.

2. A process for producing an amorphous form of rifaximin comprising crash precipitation of rifaximin from ethyl acetate with heptane.

3. The process of claim 2, further comprising milling the produced amorphous form of rifaximin.

4. A process for producing an amorphous form of rifaximin comprising lyophilization of rifaximin in p-dioxane: water 1:1, and fast evaporation from acetone.

5. The process of claim 4, further comprising milling the produced amorphous form of rifaximin.

6. A process for producing an amorphous form of rifaximin comprising precipitation of rifaximin from acetone.

7. The process of claim 6, further comprising milling the produced amorphous form of rifaximin.

* * * * *